US011957661B2

(12) United States Patent
Smith et al.

(10) Patent No.: US 11,957,661 B2
(45) Date of Patent: Apr. 16, 2024

(54) JAK1 PATHWAY INHIBITORS FOR THE TREATMENT OF VITILIGO

(71) Applicant: Incyte Corporation, Wilmington, DE (US)

(72) Inventors: Paul Smith, Wilmington, DE (US); Kurt Andrew Brown, Narberth, PA (US); Michael D. Howell, Kennett Square, PA (US); Fiona Kuo, West Chester, PA (US); James Lee, Devon, PA (US); Leandro Luiz Dos Santos, King of Prussia, PA (US); Beth Rumberger, Quarryville, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/545,377

(22) Filed: Dec. 8, 2021

(65) Prior Publication Data

US 2022/0175731 A1 Jun. 9, 2022

Related U.S. Application Data

(60) Provisional application No. 63/246,688, filed on Sep. 21, 2021, provisional application No. 63/122,574, filed on Dec. 8, 2020.

(51) Int. Cl.
*A61K 31/519* (2006.01)
*A61K 31/4155* (2006.01)
*A61K 45/06* (2006.01)
*A61P 17/00* (2006.01)

(52) U.S. Cl.
CPC ........ *A61K 31/4155* (2013.01); *A61K 31/519* (2013.01); *A61K 45/06* (2013.01); *A61P 17/00* (2018.01)

(58) Field of Classification Search
CPC .. A61K 31/4155; A61K 31/519; A61K 45/06; A61K 31/437; A61K 31/415; A61P 17/00
USPC ...................................................... 514/210.2
See application file for complete search history.

(56) References Cited

U.S. PATENT DOCUMENTS

| | | |
|---|---|---|
| 5,521,184 A | 5/1996 | Zimmerman |
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,486,902 B2 | 7/2013 | Rodgers et al. |
| 8,513,270 B2 | 8/2013 | Arvanitis et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,765,734 B2 | 7/2014 | Huang et al. |
| 8,933,085 B2 | 1/2015 | Rodgers et al. |
| 8,987,443 B2 | 3/2015 | Liu et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,249,145 B2 | 2/2016 | Rodgers et al. |
| 9,358,229 B2 | 6/2016 | Vannucchi et al. |
| 9,359,358 B2 | 6/2016 | Rodgers et al. |
| 9,382,231 B2 * | 7/2016 | Li et al. ............... C07D 403/14 |
| 9,487,521 B2 | 11/2016 | Zhou et al. |
| 9,498,467 B2 | 11/2016 | Leopold et al. |
| 9,549,916 B2 | 1/2017 | Fu et al. |
| 9,655,854 B2 | 5/2017 | Yeleswaram et al. |
| 9,802,957 B2 | 10/2017 | Zhou et al. |
| 9,926,301 B2 | 3/2018 | Li et al. |
| 9,926,601 B2 | 3/2018 | Gertler et al. |
| 9,993,480 B2 | 6/2018 | Vannucchi et al. |
| 10,166,191 B2 | 1/2019 | Ni et al. |
| 10,435,392 B2 | 10/2019 | Li et al. |
| 11,001,571 B2 | 5/2021 | Li et al. |
| 11,103,510 B2 * | 8/2021 | Montgomery et al. ..................... A61K 31/437 |
| 11,304,949 B2 | 4/2022 | Howell et al. |
| 11,591,318 B2 | 2/2023 | Li et al. |
| 2006/0106020 A1 | 5/2006 | Rodgers et al. |
| 2006/0183906 A1 | 8/2006 | Rodgers et al. |
| 2007/0135461 A1 | 6/2007 | Rodgers et al. |
| 2008/0312258 A1 | 12/2008 | Rodgers et al. |
| 2008/0312259 A1 | 12/2008 | Rodgers et al. |
| 2009/0233903 A1 | 9/2009 | Rodgers et al. |
| 2009/0318405 A1 | 12/2009 | Li et al. |

(Continued)

FOREIGN PATENT DOCUMENTS

| | | |
|---|---|---|
| CN | 101910152 | 12/2010 |
| CN | 102026999 | 4/2011 |

(Continued)

OTHER PUBLICATIONS

Rashighi M, Agarwal P, Richmond JM, Harris TH, Dresser K, Su MW, Zhou Y, Deng A, Hunter CA, Luster AD, Harris JE. CXCL10 is critical for the progression and maintenance of depigmentation in a mouse model of vitiligo. Sci Transl Med. Feb. 12, 2014;6(223) (Year: 2014).*
Desai et al Practical Dermatology, Jul. 30-31, 2020 (Year: 2020).*
Samaka et al. Clinical, Cosmetic and Investigational Dermatology 2019, 12, 469-480 (Year: 2019).*
Rothstein et al. J. Am. Acad Dermatol, 2017, 1-8 (Year: 2017).*

(Continued)

*Primary Examiner* — Yevgeny Valenrod
(74) *Attorney, Agent, or Firm* — Fish & Richardson P.C.

(57) ABSTRACT

This disclosure relates to JAK1 pathway inhibitors and their use in treating vitiligo.

13 Claims, 8 Drawing Sheets

(56) References Cited

U.S. PATENT DOCUMENTS

| | | | |
|---|---|---|---|
| 2010/0113416 | A1 | 5/2010 | Friedman et al. |
| 2010/0298334 | A1 | 11/2010 | Rodgers et al. |
| 2010/0298355 | A1 | 11/2010 | Li et al. |
| 2011/0059951 | A1 | 3/2011 | Rodgers et al. |
| 2011/0086810 | A1 | 4/2011 | Rodgers et al. |
| 2011/0207754 | A1 | 8/2011 | Li et al. |
| 2011/0224190 | A1 | 9/2011 | Huang et al. |
| 2011/0288107 | A1 | 11/2011 | Parikh et al. |
| 2012/0014968 | A1 | 1/2012 | Walsh et al. |
| 2012/0149681 | A1 | 6/2012 | Rodgers et al. |
| 2012/0149682 | A1 | 6/2012 | Rodgers et al. |
| 2013/0018034 | A1 | 1/2013 | Yao et al. |
| 2013/0045963 | A1 | 2/2013 | Rodgers et al. |
| 2013/0060026 | A1 | 3/2013 | Zhou et al. |
| 2014/0005166 | A1 | 1/2014 | Rodgers et al. |
| 2014/0121198 | A1 | 5/2014 | Li et al. |
| 2014/0135350 | A1 | 5/2014 | Ni et al. |
| 2014/0256941 | A1 | 9/2014 | Liu et al. |
| 2014/0343030 | A1* | 11/2014 | Li .................. C07D 403/14 544/405 |
| 2015/0065447 | A1 | 3/2015 | Sandor |
| 2015/0065484 | A1 | 3/2015 | Yeleswaram et al. |
| 2015/0087662 | A1 | 3/2015 | Li et al. |
| 2015/0118229 | A1* | 4/2015 | Voss et al. .......... A61K 31/4985 |
| 2015/0246046 | A1 | 9/2015 | Vaddi |
| 2015/0342952 | A1 | 12/2015 | Leopold et al. |
| 2015/0344497 | A1 | 12/2015 | Zhou et al. |
| 2016/0289215 | A1 | 10/2016 | Li et al. |
| 2018/0312492 | A1 | 11/2018 | Li et al. |
| 2019/0060311 | A1* | 2/2019 | Shanler et al. ...... A61K 31/506 |
| 2019/0175578 | A1 | 6/2019 | Koblish et al. |
| 2019/0233392 | A1 | 8/2019 | Wang et al. |
| 2019/0255053 | A1* | 8/2019 | Montgomery et al. .............. A61K 31/519 |
| 2019/0328739 | A1 | 10/2019 | Howell et al. |
| 2019/0331697 | A1 | 10/2019 | Howell et al. |
| 2020/0010456 | A1 | 1/2020 | Li et al. |
| 2020/0063188 | A1 | 2/2020 | Howell et al. |
| 2021/0238168 | A1 | 8/2021 | Li et al. |
| 2021/0380563 | A1 | 12/2021 | Zhou et al. |
| 2022/0040187 | A1 | 2/2022 | Montgomery et al. |
| 2022/0202834 | A1 | 6/2022 | Smith et al. |
| 2022/0378746 | A1 | 12/2022 | Smith et al. |
| 2023/0159501 | A1 | 5/2023 | Li et al. |

FOREIGN PATENT DOCUMENTS

| | | |
|---|---|---|
| JP | 6415543 | 10/2018 |
| WO | WO 2000009495 | 2/2000 |
| WO | WO 2000053595 | 9/2000 |
| WO | WO 2001014402 | 3/2001 |
| WO | WO 2001064655 | 9/2001 |
| WO | WO 2002000196 | 1/2002 |
| WO | WO 2003024967 | 3/2003 |
| WO | WO 2003037347 | 5/2003 |
| WO | WO 2003099771 | 12/2003 |
| WO | WO 2004005281 | 1/2004 |
| WO | WO 2004046120 | 6/2004 |
| WO | WO 2004056786 | 7/2004 |
| WO | WO 2004080980 | 9/2004 |
| WO | WO 2005028444 | 3/2005 |
| WO | WO 2006056399 | 6/2006 |
| WO | WO 2009114512 | 9/2009 |
| WO | WO 2011130146 | 10/2011 |
| WO | WO 2012068450 | 5/2012 |
| WO | WO 2012076063 | 6/2012 |
| WO | WO 2012177606 | 12/2012 |
| WO | WO 2013036611 | 3/2013 |
| WO | WO 2013040863 | 3/2013 |
| WO | WO 2014184275 | 11/2014 |
| WO | WO 2014184327 | 11/2014 |
| WO | WO 2014184328 | 11/2014 |
| WO | WO 2014184350 | 11/2014 |
| WO | WO 2017096331 | 6/2017 |
| WO | WO 2017165571 | 9/2017 |
| WO | WO 2018013918 | 1/2018 |
| WO | WO 2020191041 | 9/2020 |

OTHER PUBLICATIONS

Aikawa, "Cytokine storm in the pathogenesis of multiple organ dysfunction syndrome associated with surgical insults," Nihon Geka Gakkai Zasshi, Sep. 1996, 97(9):771-777 (English abstract only).

Algre et al., "Hypothermia and hypoglycemia induced by anti-CD3 monoclonal antibody in mice: role of tumor necrosis factor," Eur. J. Immunol., 1990, 20(3):707-710.

Argentina Office Action in Argentina Application No. 20140101971, dated Nov. 22, 2019, 6 pages.

Australian Office Action in Australian Application No. 2018223058, dated Apr. 8, 2019, 4 pages.

Australian Office Action in Australian Application No. 2018223058, Dec. 17, 2019, 4 pages.

Barabino et al., "Tear film and ocular surface tests in animal models of dry eye: uses and limitations, " Experimental Eye Research, 2004, 79: 613-621.

Beck et al., "Brief Report: Alleviation of Systemic Manifestations of Castleman's Disease by Monoclonal Anti-Interleukin-6 Antibody," N. Engl. J. Med., 1994, 330(9): 602-605.

Bennett et al., "Proposals for the classification of the myelodysplastic syndromes," British Journal of Haematology, 1982, 51: 189-199.

Berge et al., "Pharmaceutical Salts," J. Pharma. Science, 1977, 66(1): 1-19.

Bhattacharya et al., "Brittain, ed. Polymorphism in Pharmaceutical Solids," 2009, p. 327-345.

Blom et al., "Optimizing Preparative LC/MS Configurations and Methods for Parallel Synthesis Purification," J. Comb. Chem., 2003, 5: 670-683.

Blom et al., "Preparative LC-MS Purification: Improved Compound-Specific Method Optimization," J. Comb. Chem., 2004, 6: 874-883.

Blom, "Two-Pump at-Column-Dilution Configuration for Preparative Liquid Chormatography—Mass Spectrometry," J. Comb. Chem., 2002, 4: 295-301.

Bock et al. "Managing drug resistance in cancer: lessons from HIV therapy." Nature, Jul. 2012, vol. 12, pp. 494-501.

Bolen, "Nonreceptor tyrosine protein kinases", Oncogene, 1993, 8(8):2025-31.

Bollrath et al., "gp130-Meidated Stat3 Activation in Enterocytes Regulates Cell Survival and Cell-Cycle Progression during Colitis-Associated Tumorigenesis," Cancer Cell, 15: 91-102 (2009).

Borgia et al., "Features, Treatment, and Outcomes of Macrophage Activation Syndrome in Childhood-Onset Systemic Lupus Erythematosus," Arthritis Rheumatol., 2018, 70(4):616-624.

Borie et al., "Combined Use of the Jak3 Inhibitor CP-690, 550 with Mycophenolate Mofetil to Prevent Kidney Allograft Rejection in Nonhuman Primates," Transplantation, Dec. 2005, 80(12): 1756-64.

Bosworth, "JAK1/JAK2 Inhibitor Ruxolitinib Is a Rising Start," Clinical Oncology, Apr. 2011, 06:04, 3 pages.

Boudny, et al., "JAK/STAT signaling pathways and cancer", Neoplasm, 49:349-355, 2002.

Bowman, et al. "STATs in oncogenesis", Oncogene, 19:2474-2488, 2000.

Brentjens et al., "Treatment of chronic lymphocytic leukemia with genetically targeted autologous T cells: case report of an unforeseen adverse event in a phase I clinical trial," Mol Ther, 2010, 18:666-668.

Broglie et al., "Ruxolitinib for treatment of refractory hemophagocytic lymphohistiocytosis," blood advances, Aug. 22, 2017, 1(19):1533-1536.

Bromberg et al., "Inflammation and Cancer: IL-6 and STA T3 Complete the Link," Cancer Cell, 15 :79-80 (2009).

Brunning and Germing, "Myelodysplastic syndromes/neoplasms" in Chapter 5, Swerdlow, et al, eds. WHO Classification of Tumours of Haematopoietic and Lymphoid Tissues. (ed. 4th edition): Lyon, France: IARC Press, 2008, $4^{th}$ edition, pp. 88-103.

(56) References Cited

OTHER PUBLICATIONS

Bugelski et al., "Monoclonal antibody-induced cytokine-release syndrome," Expert Review of Clinical Immunology, 2009, 5(5):499-521.
Burdeinick-Kerr et al., "Noncytolytic Clearance of Sindbis Virus Infection from Neurons by Gamma Interferon Is Dependent on Jak/Stat Signaling," Journal of Virology, Apr. 2009, 83(8):3429-3435.
Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.
Burger, et al., "Gp130 and ras mediated signaling in human plasma cell line IN/a-6: a cytokine-regulated tumor model for plasmacytoma", Hematol J., 2:42-53, 2001.
Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, et al. (2002). "Molecular aspects of primary immunodeficiencies: lessons from cytokine and other signaling pathways.", J Clin Invest, 109(10): 1261-9.
Candotti, F., et al. (1997). "Structural and functional basis for JAK3-deficient severe combined immunodeficiency.", Blood, 90(10): 3996-4003.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.
Chen et al., "Blockade of interleukin-6 signaling augments regulatory T-cell reconstitution and attenuates the severity of graft-versus host disease," Blood, Jul. 2009, 114(4): 891-900.
Chen et al., "Rhinovirus Induces Airway Epithelial Gene Expression through Double-Stranded RNA and IFN-Dependent Pathways," Am J of Respir Cell and Mol Bio., Feb. 2006, 34(2):192-203.
Chen et al., "Induction of myelodysplasia by myeloid-derived suppressor cells," J Clin Invest, Nov. 2013, 123(11): 4595-611.
Chen, et al., "Stat3 Activation in Human Endometrial and Cervical Cancer", British Journal of Cancer, 96, 591-599, 2007.
Cheson et al., "Report of an international working group to standardize response criteria for myelodysplastic syndromes," Blood, Dec. 2000, 96(12): 3671-4.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Cilloni et al., "Emerging drugs for chronic myeloid leukemia", Expert Opinion on Emerging Drugs, (Jun. 2010) vol. 15, No. 2, pp. 175-184.
Claessens et al., "In vitro proliferation and differentitation of erythyroid progenitors from patients with myelodysplastic syndromes: evidence for Fas-dependent apoptosis," Blood, Mar. 2012, 1594-1601.
Clark et al., "Discovery and Development of Janus Kinase (JAK) inhibitors for Inflammatory Diseases," J Med Chem., 2014, pp. A-P.
Clinicaltrials.com, "A Study to Evaluate the Efficacy and Safety of INCB054707 in Participants With Vitiligo," NCT04818346, dated Jul. 21, 2022, 7 pages.
Coligan et al., "Current Protocols in Immunology," Wiley Press, vol. 3, 21 pages (Chapter Abstracts Only).

Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Costa Rican Office Action in Costa Rican Application No. 2015-0633, dated Feb. 25, 2020, 13 pages.
Costa Rican Office Action in Costa Rican Application No. 2015-0633, dated Sep. 20, 2019, 14 pages.
Das et al., "Janus kinase inhibition lessens inflammation and ameliorates disease in murine models of hemophagocytic lymphohistiocytosis," Blood, Jan. 29, 2016, 127(3):1666-1675.
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haema.
Deuse, T. et al., "Novel Immunosuppression: R348, a JAK3- and Syk-Inhibitor Attenuates Acute Cardiac Allograft Rejection", Transplantation, 2008, 85(6) 885-892.
Dudley et al., "A VEGF/JAK2/STAT5 axis may partially mediate endothelial cell tolerance to hypoxia," Biochem J, Sep. 2005, 390(Pt 2): 427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), A.
Eurasian Office Action in Eurasian Application No. 201592199, dated Feb. 4, 2019, 7 pages.
Eurasian Office Action in Eurasian Application No. 202390267, dated Feb. 16, 2023, 5 pages.
European Search Report in European Application No. 18215671.1, dated May 14, 2019, 5 pages.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux, et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Ferran et al., "Cytokine-related syndrome following injection of anti-CD3 monoclonal antibody: further evidence for transient in vivo T cell activation," Eur. J. Immunol., 1990, 20(3):509-515.
Ferran et al., "Inter-mouse strain differences in the in vivo anti-CD3 induced cytokine release," Clin. Exp. Immunol., 1991, 86(3):537-543.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American.
Flex et al., "Somatically acquired JAK1 mutations in adult acute lymphoblastic leukemia," J Exp Med., 2008, 205(4):751-758.
Fonesca et al., "Interleukin-6 as a key player in systemic inflammation and joint destruction," Autoimmunity Reviews, 2009, 8(7):538-542.
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13.
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA.
Fridman, Jordan et al. "Efficacy and Tolerability of Novel JAK Inhibitors in Animal Models of Rheumatoid Arthritis" poster pre-

(56) References Cited

OTHER PUBLICATIONS sented at the ACR/ARHP (American College of Rheumatology/Association of Rheumatology Health Professionals) Scientific Meeting 200.

Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (.

Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes.

Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).

Gaestel et al., "Targeting innate immunity protein kinase signalling in inflammation," Nat Rev Drug Discov., Jun. 2009, 8(6):480-99.

Gantner at al., "Concanavalin A-induced T-cell-mediated hepatic injury in mice: the role of tumor necrosis factor," Hepatology, 1995, 21(1):190-198.

Gardner et al., "Decreased Rates of Severe CRS Seen with Early Intervention Strategies for CD19 CAR-T Cell Toxicity Management," ASH 2016, Abstract #586, Dec. 5, 2016, 6 pages.

Gennaro, "Performulation," Remington's Pharmaceutical Sciences, 17th ed., Mack Publishing Company, Easton, Pa., 1985, p. 1418.

Goodman, et al., "IL-6 Signaling in Psoriasis Prevents Immune Suppression by Regulatory T Cells," J. Immunol., Sep. 2009, 183: 3170-3176.

Gorre, M.E et al., "Clinical Resistance to STI-571 Cancer Therapy Caused by BCR-ABL Gene Mutation or Amplification." Science, 293:876, 2001.

Gottlieb, A.B., et al, "Psoriasis: Emerging Therapeutic Strategies", Nat Rev Drug Disc., 4:19-34 (2005).

Grabbe, et al., "Immunoregulatory mechanisms involved in elicitation of allergic-contact hypersensitivity", Immunol Today, Jan; 19(1):37-44 (1998) (only 1 page provide and marked "best available copy").

Greenberg, "The myelodysplastic syndromes" in Hoffman, et al, eds. Hematology: Basic Principles and Practice (3rd ed.), Churchill Livingston; 2000:1106-1129.

Greene, Protective Groups in Organic Synthesis, 4th ed., John Wiley & Sons: New Jersey, (2007).

Gregory, et al., "Clinical and laboratory features of myelofibrosis and limitations of current therapies", Clinical Advances in Hematology and Oncology, (Sep. 2011) vol. 9, No. 9, pp. 1-3.

Grivennikov, et al., "IL-6 and STAT3 are required for survival of intestinal epithelial cells and the development of colitis-associated cancer", Cancer Cell, 15:103-111 (2009).

Groneberg et al., "Animal models of allergic and inflammatory conjunctivitis," Allergy, Nov. 2003, 58(11): 1101-13.

Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.

Guschin et al., "A major role for the protein tyrosine kinase JAK1 in the JAK/STAT signal transduction pathway in response to interleukin-6," Embo J, 1995, 14(7):1421-1429.

Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).

Harris et al., "World Health Organization classification of neoplastic diseases of the hematopoietic and lymphoid tissues: report of the Clinical Advisory Committee meeting-Airlie House, Virginia, Nov. 1997," J Clin Oncol, Dec. 1999, 17(12): 3835–.

Hay et al., "Kinetics and biomarkers of severe cytokine release syndrome after CD19 chimeric antigen receptor-modified T-cell therapy," Immunobio Immunother., Nov. 23, 2017, 130(21):2295-2306.

Huang, "Inhibition of STAT3 activity with AG490 decreases the invasion of human pancreatic cancer cells in vitro", Cancer Sci. 97(12):1417-23 (2006).

Indian Office Action in Indian Application No. 11174/DELNP/2015, dated Nov. 19, 2019, 8 pages.

International Preliminary Report on Patentability in International Application No. PCT/US2014/038388, dated Nov. 17, 2015, 7 pages.

International Preliminary Report on Patentability in International Application No. PCT/US2019/018066, dated Aug. 18, 2020, 8 pages.

International Search Report and Written Opinion in International Application No. PCT/US2014/038388, dated Sep. 1, 2014, 9 pages.

International Search Report and Written Opinion in International Application No. PCT/US2019/018066, dated Apr. 12, 2019, 12 pages.

International Search Report and Written Opinion in International Application No. PCT/US2021/035400, dated Aug. 12, 2021, 14 pages.

International Search Report and Written Opinion in International Application No. PCT/US2021/062419, dated Mar. 16, 2022, 15 pages.

Ishizaki, et al., "Pharmacological Properties of Y-27632, a Specific Inhibitor of Rho-Associated Kinases", Molecular Pharmacology, 2000, 57, 976-983.

Itagaki, et al, "Expedient Synthesis of Potent Cannabinoid Receptor Agonist (−)-CP55,940", Organic Letters, 2005; 7(19); 4181-4183.

Jädersten et al., "Long-term outcome of treatment of anemia in MDS with erythropoietin and G-CSF," Blood, Aug. 2005, 106(3): 803-11.

James, et al., "A unique clonal JAK2 mutation leading to constitutive signalling causes polycythaemia vera", Nature, 434 (7037):1144-8 (2005).

Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.

Japanese Office Action in Japanese Application No. 2016-514126, dated Feb. 27, 2018, 5 pages (English Translation).

Japanese Office Action in Japanese Application No. 2018-187613, dated Jan. 7, 2020, 4 pages.

Japanese Office Action in Japanese Application No. 2020-543559, dated Feb. 14, 2023, 8 pages.

Jee, et al., "Overview: animal models of osteopenia and osteoporosis", J Musculoskel. Neuron, Interact., 1(3):193-207 (2001).

Juvekar and Ruggeri, "Presentation:Preclinical Efficacy, PD and MoA Studies of Ruxolitinib and Itacitinib in Models of GVHD to Support their Clinical Development," Nov. 29, 2017, 36 pages.

Kaercher, T., "Ocular symptoms and signs in patients with ectodermal dysplasia symdromes", Grafes Arch Clin Exp Ophthalmol, 2004;495-500.

Kamb, "What's wrong with our cancer models?" Nature Reviews Drug Discovery, 2005, 4:161-165.

Kantarjian et al., "Decitabine improves patient outcomes in myelodysplastic syndromes: results of phase III randomized study," Cancer, Apr. 2006, 106(8): 1794-803.

Kato et al., "Airway Epithelial Cells Produce B Cell-Activating Factor of TNF Family by an IFN—Dependent Mechanism1," J of Immunol., Nov. 15, 2006, 177(10):7164-7172.

Kaushansky, K., "Lineage-Specific Hematopoietic Growth Factors", NEJM 354:2034-45 (2006).

Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).

Kenderian et al., "Ruxolitinib Prevents Cytokine Release Syndrome after Car T-Cell Therapy Without Impairing the Anti-Tumor Effect in a Xenograft Model," Abstracts, Biol Blood Marrow Transplant, 2017, 23:S18-S391.

Kharas, et al., "ABL Oncogenes and Phosphoinositide 3-Kinase: Mechanism of Activation and Downstream Effectors.", Cancer Res., 65(6):2047-2053, Mar. 15, 2005.

Killedar et al., "Early pathogenic events associated with Sjogren's syndrome (SjS)-like disease of the NOD mouse using microarray analysis," Lab Invest, Dec. 2006, 86(12): 1243-1260.

(56) References Cited

OTHER PUBLICATIONS

Kiss, Robert, "Recent developments on JAK2 inhibitors: A patent review", Expert Opinion on Therapeutic Patents, (Apr. 2010) vol. 20, No. 4, pp. 471-495.
Kola, "Can the pharmaceutical industry reduce attrition rates?" Nature Reviews Drug Discovery, 2004, 3:711-715.
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kudlacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai, et al., "Mechanistic Study on the Inactivation of General Acyl-CoA Dehydrogenase by a Metabolite of Hypoglycin A", J. Am. Chem. Soc. 113: 7388-7397 (1991).
Larson, "Myelodysplasia: when to treat and how," Best Pract Res Clin Haematol, 2006, 19(2): 293-300.
Lee et al., "Current concepts in the diagnosis and management of cytokine release syndrome, " Blood, May 29, 2014, 124(2):188-195.
Lemp, "The Definition and Classification of Dry Eye Disease: Report of the Definition and Classification Subcommittee of the International Eye Workshop," The Ocular Surface, 5(2): 75-92.
Léo et al., "Identification of a monoclonal antibody specific for a murine T3 polypeptide, " Proc. Natl. Acad. Sci. USA, 1987, 34:1374-1378.
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010, 30 pages.
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
List et al., "Efficacy of lenalidomide in myelodysplastic syndromes," N Engl J Med, Feb. 2005, 352(6): 549-57.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Publi.

Lübbert, et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert, et al., Low-dose decitabine versus best supportive care in elderly patients with intermediate- or high-risk myelodysplastic syndrome (MDS) ineligible for intensive chemotherapy: final results of the randomized phase III study of the European Org.
Lube et al., "Evans Syndrome at Childhood-Onset Systemic Lupus Erythematosus Diagnosis: A Large Multicenter Study," Pediatr Blood Cancer, 2016, 63:1238-1243.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia. ", J. Cellular Biochemistry (2010) LNKD-PUBMED:20014066, XP-002673720 vol. 109, No. 2 (2010) pp. 320-328.
Mascarenhas, "Primary analysis of a phase II open-label trial of CB039110, a selective JAK1 inhibitor, in patients with myelofibrosis," Haematologica. 2016, pp. 1-22 and Supplemental Data, pp. 1-7.
Maschalidi et al., "Therapeutic effect of JAK1/2 blockade on the manifestations of hemophagocytic lymphoistiocytosis in mice," Blood, May 24, 2016, 128(1):60-71.
Maude et al., "Managing Cytokine Release Syndrome Associated With Novel T Cell-Engaging Therapies, " Cancer J., 2014, 20(2):119-122.
Maxson et al., "Oncogenic CSF3R Mutations in Chronic Neutrophilic Leukemia and Atypical CML," N. Engl. J. Med., 2013, 368(19):1781-1790.
McMillan, "The systemic inflammation-based Glasgow Prognostic Score: a decade of experience in patients with cancer," Cancer Treat Rev, Aug. 2013, 39(5): 534-40.
Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6.
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117.
Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.
Mexican Office Action in Mexican Application No. MX/a/2015/015738, dated Aug. 6, 2019, 5 pages.
Meydan et al., "Inhibition of acute lymphoblastic leukaemia by a Jak-2 inhibitor", Nature. Feb. 15, 1996;379(6566):645-8.
Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Ep.
Miyoshi et al., "Interleukin-8 concentrations in conjunctival epithelium brush cytology samples correlate with neutrophil, eosinophil infiltration, and corneal damage", Cornea, 2001;20:743-7.

(56) References Cited

OTHER PUBLICATIONS

Molldrem, et al., "Antithymocyte globulin for patients with myelodysplastic syndrome," Br J Haematol, Dec. 1997, 99(3): 699-705.
Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Mullighan, "JAK mutations in high-risk childhood acute lymphoblastic leukemia," Proc Natl Acad Sci USA, 2009, 106(23):9414-9418.
Mundle et al., "Evidence for Involvement of Tumor Necrosis Factor-a in Apoptotic Death of Bone Marrow Cells in Myelodysplastic Syndromes, "Am J Hematol, 1999, 60:36-47.
Naka T., "The paradigm of IL-6: from basic science to medicine", Arthritis Res., 2002;4 Suppl 3:S233-42.
Nakagawara, Akira, "Trk receptor tyrosine kinases: A bridge between cancer and neural development." Cancer Letters, 169:107-114, 2001.
Naqvi, et al., "A potential role of ruxolitinib in leukemia", Expert Opinion on Investigational Drugs, (Aug. 2011) vol. 20, No. 8, pp. 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Neelapu et al., "Chimeric antigen receptor T-cell therapy—assessment and management of toxicities, " Nat Rev Clin Oncol., 2018, 15(1):47-62.
Neidle, Stephen, Cancer Drug Design and Discovery, (Elsevier/Academic Press, 2008) pp. 427-431.
Neubauer, H., et al., "Jak2 Deficiency Defines an Essential Developmental Checkpoint in Definitive Hematopoiesis", Cell, 93(3): 397-409 (1998).
Neuner, et al., "Increased IL-6 Production by Monocytes and Keratinocytes in Patients with Psoriasis," J. Invest. Dermatol, 1991, 97:27-33.
Nicholoff et al., "Recent Insights into the immunopathogenesis of psoriasis provide new therapeutic opportunities", J. Clin. Invest., 113; 1664-1675 (2004).
Nishimoto et. al., "Improvement in Castleman's disease by humanized anti-interleukin-6 receptor antibody theraphy," *Blood*, 2000, 95(1):56-61.
Norman, "Selective JAK1 inhibitor and selective Tyk2 inhibitor patents, " *Expert Opinion*, Informa Healthcare. 2012, available at: <http://informahealthcare.com/dol/pdfplus/10.1517/13543776.2012. 723693>.
Ortmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.
Park et al., "CP-690550, a Janus Kinase Inhibitor, Suppresses CD4 T-Cell-Mediated Acute Graft-Versus-Host Disease by Inhibiting the Interferon-y Pathway, "Transplantation, 2010, 90(8):825-835.
Park et al., "Homogeneous proximity tyrosine kinase assays: scintillation proximity assay versus homogeneous time-resolved fluorescence," Analytical Biochemistry, 1999, 269(1):94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Of.

Pedranzini et al., "Pyridone 6, a pan-Janus-activated kinase inhibitor, induces growth inhibition of multiple myeloma cells, " Cancer Res., 2006, 66(19):9714-9721.
Pernis, et al., "JAK-STAT signaling in asthma." J Clin Invest, 109(10): 1279-83 (2002).
Persaud et al., "Plasma pharmacokinetics and distribution of ruxolitinib into skin following oral and topical administration in minipigs," Int J Pharm., Nov. 30, 2020, 590:119889.
Peruvian Office Action in Peruvian Application No. 2406-2015, dated Sep. 26, 2019, 17 pages.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 1.
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby–.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Soc.
Rashighi et al., " CXCL10 is critical for the progression and maintenance of depigmentation in a mouse model of vitiligo," Sci Ttansl Med. Feb. 2014, 6(223):233ra23.
Raza et al., "Novel insights into the biology of myelodysplastic syndromes: excessive apoptosis and the role of cytokines, " Int J Hematol, Jun. 1996, 63(4): 265-78.
Raza et al., "The myelodysplastic syndromes in 1996: complex stem cell disorders confounded by dual actions of cytokines," Leuk Res, Nov.-Dec. 1996, 20(11-12): 881-90.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Remington's Pharmaceutical Sciences, 17th ed., Mack Publishing Company, Easton, Pa., 1985, p. 1418.
Roberts et al., "Trends in the risks and benefits to patients with cancer participating in phase 1 clinical trials," JAMA, Nov. 2004, 292(17): 2130-40.
Roche, "Bioreversible Carriers in Drug Design," American Pharmaceutical Association and Pergamon Press, 1987, Front Matter Only, 4 pages.
Rodig, et al., "Disruption of the Jak1 gene demonstrates obligatory and nonredundant roles of the Jaks in cytokine-induced biologic responses." Cell, 93(3): 373-83 (1998).
Roudebush et al., "Pharmacologic manipulation of a four day murine delayed type hypersensitivity model," Agents Actions, Jan. 1993, 38(1-2): 116-21.
Rousvoal, G. et al. "Janus kinase 3 inhibition with CP-690,550 prevents allograft vasculopathy", Transpl Int., 2006 19(12):1014-21.
Samanta et al., "Janus kinase 2: a critical target in chronic myelogenous leukemia", Cancer Res. Jul. 1, 2006;66(13):6468-72.
Schiffer, "Clinical issues in the management of patients with myelodysplasia," Hematology Am Soc Hematol Educ Program, 2006: 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling," Adv Pharmacol. 2000; 47:113-74.
Schrader et al., "Animal models of dry eye," Dev Opthalmol, 2008, 41:298-312.
Schram et al., "How I treat hemophagocytic lymphohistiocytosis in the adult patient ," Blood, 2005, 125(19):2908-2914.
Science IP Search Report, Mar. 2021, 421 pages.
Scott, et al., "Jaks, STATs, Cytokines, and Sepsis." Clin Diagn Lab Immunol, 9(6):1153-9 (2002).

(56) References Cited

OTHER PUBLICATIONS

Search Report ID SR-20210895.01, "Single Crystal Structure Determination of INCB054707 Phosphate," dated May 20, 2021, 42 pages.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimizu et al., "Distinct cytokine profile in juvenile systemic lupus erythematosus-associated macrophage activation syndrome,"Clin Immunol., Feb. 2013, 146(2):73-76.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Singh, et al., "Serum concentration of IL-6, IL-2, TNF-α, and IFNγ in Vitiligo patients, " Indian J Dermatology., Jan.-Feb. 2012, 57(1):12-14.
Sloand et al., "Factors affecting response and survival in patients with myelodysplasia treated with immunosuppressive therapy," J Clin Oncol, May 2008, 26(15): 2505-11.
Smith et al., "Basic pathogenic mechanisms operating in experimental models of acute anteriior uveitis," Immunol Cell Biol, Dec. 1998, 76(6): 497-512.
Smolen et al., "Effect of interleukin-6 receptor inhibition with tocilizumab in patients with rheumatoid arthritis (Option study): a double-blind, placebo-controlled, randomised trial," Lancet, 2008, 371:987-997.
Smolen, et al, "Effect of interleukin-6 receptor inhibition with tocilizumab in patients with rheumatoid arthritis (Option study): a double-blind, placebo-controlled, randomized trial", Lancet 371:987, 2008 (2008).
Snodgrass et al., "Cytokine Release Syndrome: CD19-directed CAR T cell therapy, Bispecifics & Haploidentical HSCT," Nov. 22, 2017, 33 pages.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, Jun. 2014, 123(24): 3832-42.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol Chem, May 2004, 279(19):19936-47.
Staerk, J., et al., "JAK1 and Tyk2 activation by the homologous polycythemia vera JAK2 V617F mutation: cross-talk with IGF1 receptor", J Biol Chem., 280:41893-41899 (2005).
Stirewalt et al., "Predictors of relapse and overall survival in Philadelphia chromosome-positive acute lymphoblastic leukemia after transplantation", Biol Blood Marrow Transplant. Mar. 2003;9(3):206-12.

Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Symington et al., "The relationship of serum IL-6 levels to acute graft-versus-host disease and hepatorenal disease after human bone marrow transplantation," Transplantation, Sep. 1992, 54(3): 457-62.
Takemoto, et al. (1997). "Proliferation of adult T cell leukemia/lymphoma cells is associated with the constitutive activation of JAK/STAT proteins." Proc Natl Acad Sci U S A, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Taylor et al., "The JAK1-Selective Inhibitor Filgotinib Displays an Anti-Inflammatory Biomarker Signature in Rheumatoid Arthritis Patients," 2016 ACR/ARHP Annual Meeting, Abstract No. 2616, Sep. 28, 2016.
Teachey et al., "Identification of Predictive Biomarkers for Cytokine Release Syndrome after Chimeric Antigen Receptor T cell Therapy for Acute Lymphoblastic Leukemia," Cancer Discov. 6, 664-679 (2016).
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Decembe.
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Tisoncik et al., "Into the Eye of the Cytokine Storm," Microbiology and Molecular Biology Reviews, Mar. 2012, 76(1):16-32.
Toyonaga, "Blockade of constitutively activated Janus kinase/signal transducer and activator of transcription-3 pathway inhibits growth of human pancreatic cancer", Cancer Lett. 201(1):107-16 (2003).
Trikha et al., "Targeted anti-interleukin-6 monoclonal antibody therapy for cancer: a review of the rationale and clinical evidence," Clinical Cancer Research, 2003, 9:4653-4665.
Vanhoutte, "Selective JAK1 Inhibition in the Treatment of Rheumatoid Arthritis: Proof of Concept with GLPG0634,"Arthritis Rheum 64.10 (2012): S1051-1.
Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 page.
Vannucchi, A. et al., "Inhibitorsof PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 A.
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abs.
Vardiman et al., "The 2008 revision of the World Health Organization (WHO) classification of myeloid neoplasms and acute leukemia: rationale and important changes, " Blood, Jul. 2009, 114(5): 937-51.
Vardiman et al., "The World Health Organization (WHO) classification of the myeloid neoplasms," Blood, Oct. 2002, 100(7): 2292-302.
Verma, et al., "Jak family of kinases in cancer", Cancer and Metastasis Reviews, vol. 22, No. 4, 423-434, DOI: 10.1023/A:1023805715476 (2003).
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.

(56) References Cited

OTHER PUBLICATIONS

Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of He.
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #04.
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), p.
Verstovsek, Srdan et al., Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL.
Vietnamese Office Action in Vietnamese Application No. 11-2019-01578, dated Apr. 26, 2019, 2 pages.
Wagh et al., "Polymers used in ocular dosage form and drug delivery systems," Asian J. Pharma, 12-17.
Williams, et al. "Initial Efficacy of INCB018424, a selective Janus Kinase1 & 2 (JAK1&2) Inhibitor in Rheumatoid Arthritis (RA)," European League Against Rheumatism (EULAR) meeting presentation and abstract (Jun. 11-14, 2008, Paris, France). Annals Rheum.
www.quora.com, "What is a 'cytokine storm,' and what are the diseases that cause that?", retrieved on Feb. 18, 2018, retrieved from URL <https://www.quora.com/What-is-a-cytokine-storm-and-what-are-the-diseases-that-cause-that>, 9 pages.
Xiaoyang et al., "Knockdown of STAT3 Expression by RNA Interference Inhibits the Induction of Breast Tumors in Immunocompetent Mice", Cancer Res Apr. 1, 2005 65; 2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Xu et al., "Cytokine release syndrome in cancer Immunotherapy with chimeric antigen receptor engineered T cells," Cancer Lett., 2014, 343(2):172-178.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Yongjun et al., "Advances in research of tyrosine kinases inhibitor of vascular endothelial growth factor receptor," Chinese J New Drugs, Dec. 31, 2008, 17(7):544-550.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," Journal of Clinical Oncology, Nov. 2012, 30(33): 4161-4167.
Yu, et al., "Constitutive activation of the Janus kinase-STAT pathway in T lymphoma overexpressing the Lck protein tyrosine kinase", J Immunol. 159(11):5206-10 (1997).
Zhang et al., "An analytical biomarker for treatment of patients with recurrent B-ALL after remission induced by infusion of anti-CD19 chimeric antigen receptor T (CAR-T) cells," Sci China Life Sci., Apr. 2016, 59(4):379-385.
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zou, et al., "Signaling Pathways Activated by Oncogenic Forms of Abl Tyrosine Kinase." Journal of Biological Chemistry, 274(26):18141-18144, 1999.
Liu et al., "Cytokines: From Clinical Significance to Quantification," Adv. Sci., Aug. 2021, 8(15):1-29.
Raman et al., "Chemokines in health and disease," Exp Cell Res., Mar. 10, 2011, 317(5):575-589.
European Office Action in European Application No. 19707655.7, dated Jun. 26, 2023, 6 pages.
Gonzales et al., "Oclacitnib (Apoquel) is a novel Janus Kinase inhibitor with activity against cytokines involved in allergy," Journal of Veterinary Pharmacology and Therapeutics, Aug. 1, 2014, 37(4):317-324.
Harlgai et al., "Selectivity of Janus Kinase Inhibitors in Rheumatoid Arthritis and Other Immune-Mediated Inflammatory Diseases: Is Expectation the Root of All Headache?" Drugs, 2020, 80:1183-1201.
Meyer et al., "Anti-inflammatory activity and neutrophil reductions mediated by the JAK1/JAK3 inhibitor, CP-690,550, in rat adjuvant-induced arthritis, " Journal of Inflammation, Jan. 1, 2010, pp. 1-12.
Petri et al., "Baricitinib for systemic lupus erythematosus: a doubleblind, randomised, placebo-controlled, phase 3 trial (SLE-BRAVE-II)," Lancet, 2023, 401:1011-19.
Traves et al., "JAK selectivity and the implications for clinical inhibition of pharmacodynamic cytokine signalling by filgotinib, upadacitinib, tofacitinib and baricitinib," Ann Rheum Dis, 2021, 80:865-875.
Zhang et al., "The efficacy and safety of tofacitinib, peficitinib, solcitinib, baricitinib, abrocitinib and deucravacitinib in plaque psoriasis—A network meta-analysis," JEADV, 2022, 36:1937-1946.

\* cited by examiner

IFN – interferon
IL – interleukin
CXCL10 - Interferon gamma-induced protein 10 (IP-10)

*p < 0.05
***p < 0.001

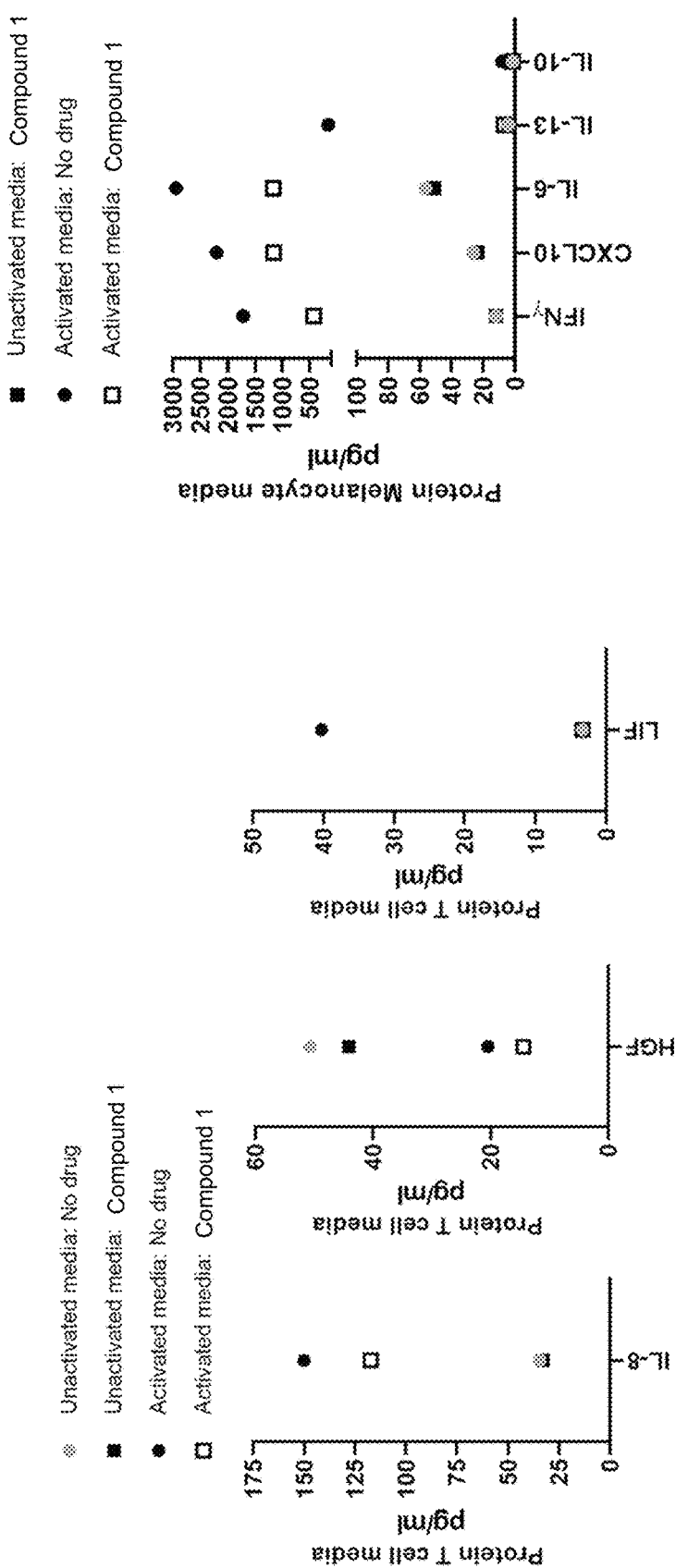

IFN - interferon
IL - interleukin
CXCL10 - interferon gamma-induced protein 10 (IP-10)

** p < 0.01

JAK1 PATHWAY INHIBITORS FOR THE TREATMENT OF VITILIGO

PRIORITY CLAIM

This application claims the benefit of priority of U.S. Provisional Application Nos. 63/122,574, filed Dec. 8, 2020, and 63/246,688, filed Sep. 21, 2021, each of which is incorporated herein by reference in its entirety.

TECHNICAL FIELD

This disclosure relates to JAK1 pathway inhibitors and the use thereof in treating vitiligo.

BACKGROUND

Vitiligo is a chronic skin disorder characterized by depigmented patches of skin due to autoimmune destruction of melanocytes and is estimated to affect 0.5-2.0% of the global population (varying geographically). Vitiligo prevalence is similar between men and women, and there is no known difference in presentation based on skin type or race. Average age of onset is mid-twenties, but can occur at any age. The disorder tends to progress over time. 15-25% of people with vitiligo also tend to have at least one other autoimmune disorder. Non-segmental vitiligo is the most common subtype (up to 90% of vitiligo patients) and is characterized by symmetric bilateral white patches. The white patches are typically found on hands, feet and perioral/face.

There is a potential significant impact to quality of life for someone suffering from vitiligo due to psychosocial factors. The chronic nature of vitiligo and lack of effective therapy can have a negative psychosocial impact on patients, affecting quality of life similarly to other dermatological diseases. Involvement of cosmetically-sensitive areas, such as the face and hands, can have a major impact on self-esteem and eventually link to the psychological burden and quality of life; individuals with more than 25% of body surface area involvement may have difficulties performing daily tasks such as gardening, shopping, or clothing selection, and difficulty in socialization, like participating in sports activities and initiating and maintaining romantic relationships.

Clinical management aims to halt depigmentation and induce repigmentation. No drugs are currently approved for the treatment of patients with vitiligo. In general, first-line treatment consists of off-label use of topical corticosteroids and calcineurin inhibitors. Second line treatment consists of phototherapy (narrow-band UVB and psoralen and UVA) and systemic corticosteroids. Less common therapies include surgical grafting techniques and depigmenting treatments. Accordingly, there is a need to develop new therapies for the treatment of vitiligo. This application addresses this need and others.

DESCRIPTION OF THE DRAWINGS

FIGS. 3A-C are graphs depicting the effect of Compound 1 on growth factors and chemokine using T-cell compartments, protein T cell media (pg/ml) vs. IL-8 (A), HGF (B), and LIF (C).

FIG. 4 is a graph depicting the effect of Compound 1 on JAK1-dependent cytokines using melanocytes, protein melanocyte media (pg/ml) vs. specific JAK1-dependent cytokines.

SUMMARY

Figure 2:
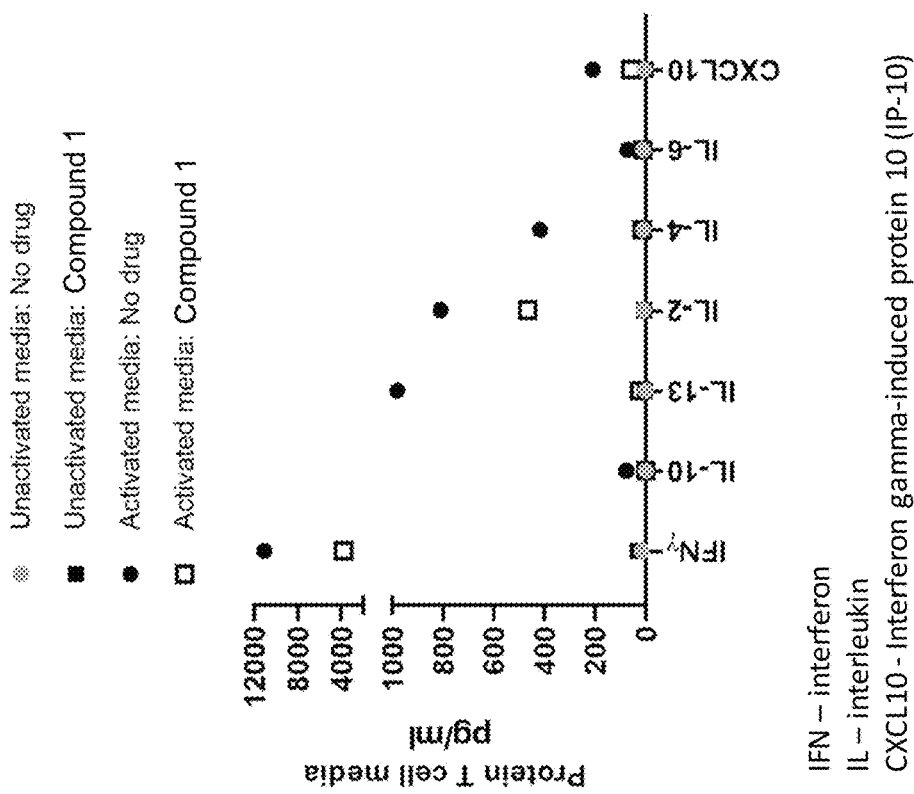
FIG. 2 is a graph depicting the effect of Compound 1 on JAK1-dependent cytokines using T-cell compartments, protein T cell media (pg/ml) vs. specific JAK1-dependent cytokines.

Provided herein are methods for the treatment of vitiligo in a subject in need thereof, comprising administering to the subject a therapeutically effective amount of a JAK1 pathway inhibitor, or a pharmaceutically acceptable salt thereof.

Provided herein is a JAK1 pathway inhibitor, or a pharmaceutically acceptable salt thereof, for the treatment of vitiligo in a subject in need thereof.

Provided herein is a use of a JAK1 pathway inhibitor, or a pharmaceutically acceptable salt thereof, for manufacture of a medicament for use in treating vitiligo in a subject in need thereof.

DETAILED DESCRIPTION

The present invention provides, inter alia, a method of treating vitiligo in a subject in need thereof, comprising administering to the subject a therapeutically effective amount of a JAK1 pathway inhibitor, or a pharmaceutically acceptable salt thereof. In some embodiments, the vitiligo is non-segmental vitiligo.

In some embodiments, the present invention provides a method for treating vitiligo in a subject, said method comprising administering to the subject a therapeutically effective amount of a JAK1 pathway inhibitor, or a pharmaceutically acceptable salt thereof.

In some embodiments, the JAK1 pathway inhibitor, or a pharmaceutically acceptable salt thereof, is selective for JAK1 over JAK2, JAK3, and Tyk2.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

In some embodiments, the vitiligo is non-segmental vitiligo.

In some embodiments, the JAK1 pathway inhibitor, or pharmaceutically acceptable salt thereof, is administered in a daily dose of about 5 mg to about 95 mg on a free base basis.

In some embodiments, the JAK1 pathway inhibitor, or pharmaceutically acceptable salt thereof, is administered in a daily dose of about 15 mg, about 45 mg, 75 mg, or about 90 mg on a free base basis.

In some embodiments, the JAK1 pathway inhibitor, or pharmaceutically acceptable salt thereof, is administered in combination with a further therapeutic agent.

In some embodiments, the further therapeutic agent comprises a Janus kinase inhibitor.

In some embodiments, the Janus kinase inhibitor comprises ruxolitinib, or a pharmaceutically acceptable salt thereof.

In some embodiments, the administering comprises administering the JAK1 pathway inhibitor, or pharmaceutically acceptable salt thereof, together with at least one pharmaceutically acceptable carrier or excipient.

In some embodiments, the vitiligo is non-segmental vitiligo. Non-segmental vitiligo is associated with some form of symmetry in the location of the patches of depigmentation. Classes of non-segmental vitiligo include generalized vitiligo, universal vitiligo, acrofacial vitiligo, mucosal vitiligo, and focal vitiligo. In some embodiments, the vitiligo is generalized vitiligo. In some embodiments, the vitiligo is universal vitiligo. In some embodiments, the vitiligo is acrofacial vitiligo. In some embodiments, the vitiligo is mucosal vitiligo. In some embodiments, the vitiligo is focal vitiligo. Generalized vitiligo, the most common category, affects approximately 0.5% of the world's population, with an average age of onset at about 24 years and occurring with approximately equal frequencies in males and females. While there is no variation by ethnicity, the disease can be much more apparent and thus emotionally distressing for individuals with darker skin colors.

In some embodiments, the vitiligo is segmental vitiligo. Segmental vitiligo differs in appearance, cause and prevalence than non-segmental vitiligo. Segmental vitiligo tends to affect areas of skin that are associated with dorsal roots from the spinal cord and is most often unilateral. Segmental vitiligo spreads much more rapidly than non-segmental vitiligo and, without treatment, segmental vitiligo is much more stable/static in course and is not associated with auto-immune diseases.

In some embodiments, efficacy of the treatment method disclosed herein can be established based upon percent change from various baseline measurements using various indicators. For example, total % of depigmented body surface area (BSA), including facial and nonfacial areas can be used. BSA can be assessed by the Palmar Method, as follows: the approximate size of the subject's entire palmar surface (ie, the palm plus 5 digits) should be considered 1% BSA, and the approximate size of the subject's thumb should be considered 0.1% BSA.

As used herein, the term "Face" may be generally defined as including the area on the forehead to the original hairline, on the cheek to the jawline vertically to the jawline and laterally from the corner of the mouth to the tragus. The area "Face" does not include surface area of the lips, scalp, ears, or neck but includes the nose and eyelids.

In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% reduction of depigmented Total Body Surface Area (T-BSA) in a subject.

In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% reduction of depigmented Facial Body Surface Area (F-BSA) in a subject.

In some embodiments, areas affected by depigmentation due to vitiligo can be assessed using the Vitiligo Area Scoring Index (VAST). VASI is based on a composite estimate of the percentage of vitiligo involvement (% BSA, using the Palmar Method) and the degree of depigmentation within the vitiligo lesions. In some embodiments, the degree of depigmentation can be determined and estimated to the nearest of the following percentages: 0%, 10%, 25%, 50%, 75%, 90%, or 100%. At 100% depigmentation, no pigment is present; at 90%, specks of pigment are present; at 75%, the depigmented area exceeds the pigmented area; at 50%, the depigmented and pigmented area are equal; at 25%, the pigmented area exceeds the depigmented area; at 10%, only specks of depigmentation are present. At 0% depigmentation, no depigmentation is present.

In some embodiments, the Facial Vitiligo Area Scoring Index (F-VASI) is then derived by multiplying the percentage of facial vitiligo involvement (% F-BSA) and the degree of depigmentation within the vitiligo lesions, and summing the values of all lesions together.

In some embodiments, efficacy may be measured using Total body VASI (T-VASI) which is derived by multiplying the percentage of total body vitiligo involvement (% T-BSA) and the degree of depigmentation within the vitiligo lesions for all body sites, and summing the values of all sites together (possible range, 0 to 100). For the purposes of T-VASI assessment, the body is divided into the following 6 separate and mutually exclusive sites: (1) head/neck (including scalp), (2) hands, (3) upper extremities (including axillae and excluding hands), (4) trunk (including genitalia, excluding buttocks), (5) lower extremities (including buttocks and excluding feet), and (6) feet.

In some embodiments, efficacy can be evaluated based upon percent change from baseline of T-VASI. In some embodiments, a JAK1 inhibitor, e.g., Compound 1, and/or methods of use described herein result in a reduction of T-VASI in a subject. In some embodiments, a JAK1 inhibitor, e.g., Compound 1, and/or methods of use described herein result in about a 50% or greater reduction of T-VASI in a subject. In some embodiments, a JAK1 inhibitor, e.g., Compound 1, and/or methods of use described herein result in about a 75% or greater reduction of T-VASI in a subject. In some embodiments, a JAK1 inhibitor, e.g., Compound 1, and/or methods of use described herein result in about a 90% or greater reduction of T-VASI in a subject. In some embodiments, a JAK1 inhibitor, e.g., Compound 1, and/or methods of use described herein result in about a 40% to about a 90% or greater reduction of T-VASI in a subject. In some embodiments, a JAK1 inhibitor, e.g., Compound 1, and/or methods of use described herein result in about a 50% to about a 95% or greater reduction of T-VASI in a subject. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% reduction of T-VASI in a subject.

In some embodiments, efficacy can be evaluated based upon the proportion of subjects achieving about a 50% or greater reduction of T-VASI within a certain time period. In some embodiments, efficacy can be evaluated based upon the proportion of subjects achieving about a 50% or greater, about a 75% or greater, or about a 90% or greater reduction of T-VASI within a certain time period.

In some embodiments, efficacy can be evaluated based upon percent change from baseline of F-VASI. In some embodiments, a JAK1 inhibitor, e.g., Compound 1, and/or methods of use described herein result in a reduction of F-VASI in a subject. In some embodiments, a JAK1 inhibitor, e.g., Compound 1, and/or methods of use described herein result in about a 50% or greater reduction of F-VASI in a subject. In some embodiments, a JAK1 inhibitor, e.g., Compound 1, and/or methods of use described herein result in about a 75% or greater reduction of F-VASI in a subject. In some embodiments, a JAK1 inhibitor, e.g., Compound 1, and/or methods of use described herein result in about a 90% or greater reduction of F-VASI in a subject. In some embodiments, a JAK1 inhibitor, e.g., Compound 1, and/or methods of use described herein result in about a 40% to about a 90% or greater reduction of F-VASI in a subject. In some embodiments, a JAK1 inhibitor, e.g., Compound 1, and/or methods of use described herein result in about a 50% to about a 95% or greater reduction of F-VASI in a subject. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% reduction of F-VASI in a subject.

The Vitiligo Extent Score (VES) can be a validated measure to express the overall vitiligo involvement of the body. The VES uses pictures of 19 separate anatomical areas for assessment of vitiligo extent (% BSA).

The Vitiligo Extent Score-plus (VESplus) can be a validated measure to express the overall vitiligo involvement of the body and a scale to assess the perifollicular repigmentation pattern. The VESplus uses pictures of 19 separate areas for assessment of vitiligo extent (% BSA) and their respective pattern of perifollicular repigmentation, divided in 7 categories: 0%, 5%, 10%, 25%, 50%, 75% and 90%.

In some embodiments, efficacy can be evaluated based upon improvement in the vitiligo extent and perifollicular repigmentation pattern using VESplus. Typically VESplus uses the calculation of the BSA times the degree of perifollicular repigmentation. In some embodiments, a JAK1 inhibitor, e.g., Compound 1, and/or methods of use described herein result in an improvement of VESplus for a subject. In some embodiments, a JAK1 inhibitor, e.g., Compound 1, and/or methods of use described herein result in a VESplus of about 50% or greater in a subject. In some embodiments, a JAK1 inhibitor, e.g., Compound 1, and/or methods of use described herein result in a VESplus of about 75% or greater in a subject. In some embodiments, a JAK1 inhibitor, e.g., Compound 1, and/or methods of use described herein result in a VESplus of about 90% or greater in a subject. In some embodiments, a JAK1 inhibitor, e.g., Compound 1, and/or methods of use described herein result in a VESplus of about 50% to about 90% or greater in a subject. In some embodiments, a JAK1 inhibitor, e.g., Compound 1, and/or methods of use described herein result in a VESplus of about 5% to about 75% or greater in a subject. In some embodiments, a JAK1 inhibitor, e.g., Compound 1, and/or methods of use described herein result in a VESplus of about 5% to about 90% or greater in a subject.

In some embodiments, efficacy can be evaluated based upon improvement in the Facial Static Investigator Global Assessment (FSIGA) score. The severity of facial vitiligo can be assessed using the FSIGA, which has a 5-point scale (Table 1).

TABLE 1

| Score | Severity | Description |
|---|---|---|
| 0 | Clear | No signs of vitiligo |
| 1 | Almost Clear | Faint, barely detectable loss of pigmentation mainly located on forehead, periocular skin, lips, and/or limited areas; approximately 90% pigmentation within lesions; no or rare signs of Koebner phenomenon, confetti-like or trichrome lesions may be present |
| 2 | Mild Vitiligo | Mild loss of pigmentation mainly located on forehead, periocular skin, lips, and/or limited areas; approximately 75% pigmentation within lesions; few signs of Koebner phenomenon, confetti-like or trichrome lesions may be present |
| 3 | Moderate Vitiligo | Moderate loss of pigmentation affecting several areas of the face with large patches; approximately 50% pigmentation within lesions; moderate number of signs of Koebner phenomenon, confetti-like or trichrome lesions may be present |
| 4 | Severe Vitiligo | Extensive loss of pigmentation affecting most areas of the face; approximately 25% or less pigmentation within lesions; many signs of Koebner phenomenon, confetti-like or trichrome lesions affecting several areas of the body may be present |

In some embodiments, a JAK1 inhibitor, e.g., Compound 1, and/or methods of use described herein result in a FSIGA score of clear (0) or almost clear (1) in a subject. In some embodiments, a JAK1 inhibitor, e.g., Compound 1, and/or methods of use described herein result in a FSIGA score improvement of at least 2 points. In some embodiments, a JAK1 inhibitor, e.g., Compound 1, and/or methods of use described herein result in a FSIGA score of clear (0) or almost clear (1) and at least a 2-point improvement in a subject.

In some embodiments, efficacy can be evaluated based upon improvement in the Static Investigator Global Assessment (SIGA) score. The severity of vitiligo can be assessed using the SIGA, which has a 5-point scale (Table 2).

TABLE 2

| Score | Severity | Description |
|---|---|---|
| 0 | Clear | No signs of vitiligo |
| 1 | Almost Clear | Faint, barely detectable loss of pigmentation mainly located on dorsal hands, feet, bony prominences, and/or limited areas; approximately 90% pigmentation within lesions; no or rare signs of Koebner phenomenon, confetti-like or trichrome lesions may be present |
| 2 | Mild Vitiligo | Mild loss of pigmentation mainly located on dorsal hands, feet, bony prominences, and/or limited areas; approximately 75% pigmentation within lesions; few signs of Koebner phenomenon, confetti-like or trichrome lesions may be present |
| 3 | Moderate Vitiligo | Moderate loss of pigmentation affecting several areas of the body with large patches; approximately 50% pigmentation within lesions; moderate number of signs of Koebner phenomenon, confetti-like or trichrome lesions may be present |
| 4 | Severe Vitiligo | Extensive loss of pigmentation affecting most areas of the body; approximately 25% or less pigmentation within lesions; many signs of Koebner phenomenon, confetti-like or trichrome lesions affecting several areas of the body may be present |

In some embodiments, a JAK1 inhibitor, e.g., Compound 1, and/or methods of use described herein result in a SIGA score of clear (0) or almost clear (1) in a subject. In some embodiments, a JAK1 inhibitor, e.g., Compound 1, and/or methods of use described herein result in a SIGA score improvement of at least 2 points. In some embodiments, a JAK1 inhibitor, e.g., Compound 1, and/or methods of use described herein result in a SIGA score improvement of at least 1, 2, or 3 points. In some embodiments, a JAK1 inhibitor, e.g., Compound 1, and/or methods of use described herein result in a SIGA score of clear (0) or almost clear (1) and at least a 2-point improvement in a subject.

Vitiligo is characterized by a progressive loss of functional melanocytes and associated with auditory abnormalities, including sensorineural hearing loss (SNHL) with a prevalence ranging from 4.0 to 68.8% when compared to healthy controls. During embryogenesis, precursor melanocyte cells (melanoblasts) migrate to the dermis, and also to the base of the cochlea, which is responsible for hearing high frequencies. It appears that inner ear melanocytes are very important for cochlear hair cell function and normal hearing. Persons suffering can undergo SNHL assessment at baseline to assess hearing, and throughout treatment to ascertain potential improvement in hearing relative to JAK1 inhibitor, e.g., Compound 1, exposure. In some embodiments, efficacy can be evaluated based upon improvement in a subject's hearing. In some embodiments, a JAK1 inhibitor, e.g., Compound 1, and/or methods of use described herein result in an improvement in a subject's baseline hearing parameters.

In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's baseline hearing parameters. In some embodiments, a JAK1 inhibitor, e.g., Compound 1, and/or methods of use described herein result in about a 50% or greater improvement in a subject's baseline hearing parameters.

In some embodiments, efficacy can be evaluated based upon improvement in a subject's response to a color-matching question (i.e., patient-reported outcomes (PROs)). In some embodiments, a JAK1 inhibitor, e.g., Compound 1, and/or methods of use described herein result in an improvement in a subject's response to a color-matching question. For the color-matching question the current subject' facial image (subjects may use a mirror) can be shown to the subject for reference, and the subject is asked to respond to the following query: "At this point of your treatment, how well does your skin color match between your face treated vitiligo skin and face normal skin?" Possible responses are: (1) Excellent, (2) Very good, (3) Good, (4) Poor, and (5) Very poor. In some embodiments, a JAK1 inhibitor, e.g., Compound 1, and/or methods of use described herein result in an improvement to the color-matching question of at least 2 points. In some embodiments, a JAK1 inhibitor, e.g., Compound 1, and/or methods of use described herein result in an improvement to the color-matching question of at least 1, 2, or 3 points.

In some embodiments, efficacy can be evaluated based upon improvement in a subject's assessed response, PRO, to a baseline facial photograph. In some embodiments, a JAK1 inhibitor, e.g., Compound 1, and/or methods of use described herein result in an improvement in a subject's assessed response to a baseline facial photograph. The Vitiligo Noticeability Scale (VNS) is a patient-reported measure of vitiligo treatment success, which has a 5-point scale. The baseline facial photograph can be shown to the subject for reference and a mirror can be provided for the subject to assess the vitiligo on their face. The subject can be asked to respond to the following query: "Compared with before treatment, how noticeable is the vitiligo now?" Possible responses are: (1) More noticeable, (2) As noticeable, (3) Slightly less noticeable, (4) A lot less noticeable, and (5) No longer noticeable. Compared with before treatment, how noticeable is the vitiligo now? Responses: (1) More noticeable, (2) As noticeable, (3) Slightly less noticeable, (4) A lot less noticeable, and (5) No longer noticeable. In some embodiments, a JAK1 inhibitor, e.g., Compound 1, and/or methods of use described herein result in a VNS score of 4 or 5.

In some embodiments, efficacy can be evaluated based upon improvement in a subject's response, PRO, to a Facial Patient Global Impression of Change-Vitiligo (F-PaGIC-V). In some embodiments, a JAK1 inhibitor, e.g., Compound 1, and/or methods of use described herein result in an improvement in a subject's response to F-PaGIC-V. The F-PaGIC-V is an assessment of improvement. It is a 7-point scale comparing the vitiligo areas at baseline with the subject's treated areas of facial vitiligo. The baseline photograph and current subjects' facial image (subject can be provided a mirror) will be shown to the subject for reference. The subject can be asked to respond to the following query: Since the start of the treatment you've received in this study, your vitiligo on your face treated with the study drug is: (1) Very much improved, (2) Much improved, (3) Minimally improved, (4) No change, (5) Minimally worse, (6) Much worse, and (7) Very much worse. In some embodiments, Compound 1 and/or methods of use described herein result in a F-PaGIC-V score of 1 or 2.

In some embodiments, efficacy can be evaluated based upon improvement in a subject's response, PRO, to a Total body Patient Global Impression of Change-Vitiligo (T-PaGIC-V). In some embodiments, a JAK1 inhibitor, e.g., Compound 1, and/or methods of use described herein result in an improvement in a subject's response to T-PaGIC-V. The T-PaGIC-V is an assessment of improvement. It is a 7-point scale comparing the vitiligo areas at baseline with the subject's treated areas of total body vitiligo. The subject can be asked to respond to the following query: Since the start of the treatment you've received in this study, your vitiligo on your total body treated with the study drug is: (1) Very much improved, (2) Much improved, (3) Minimally improved, (4) No change, (5) Minimally worse, (6) Much worse, and (7) Very much worse. In some embodiments, a JAK1 inhibitor, e.g., Compound 1, and/or methods of use described herein result in a T-PaGIC-V score of 1 or 2.

In some embodiments, efficacy can be evaluated based upon improvement, PRO, in a subject's Self-Assessment Vitiligo Extent Score (SA-VES). In some embodiments, a JAK1 inhibitor, e.g., Compound 1, and/or methods of use described herein result in an improvement in a subject's response to SA-VES from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to SA-VES from baseline. The Self-Assessment Vitiligo Extent Score (SA-VES) can be a validated tool that allow patients to select the extent of the disease (presented via images) across 12 anatomical areas.

In some embodiments, efficacy can be evaluated based upon improvement, PRO, in a subject's Vitiligo Quality of Life (VitiQoL). In some embodiments, a JAK1 inhibitor, e.g., Compound 1, and/or methods of use described herein result in an improvement in a subject's response to VitiQoL from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to VitiQoL from baseline. VitiQoL is a 15-item quality-of-life assessment that asks subjects to rate various aspects of their condition during the past month using a 7-point scale ("Not at all" to "All of the time").

In some embodiments, efficacy can be evaluated based upon improvement, PRO, in a subject's Dermatology Life Quality Index (DLQI). In some embodiments, a JAK1 inhibitor, e.g., Compound 1, and/or methods of use described herein result in an improvement in a subject's response to DLQI from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to DLQI from baseline. The DLQI is a 10-question validated questionnaire to measure how much the skin problem has affected the subject over the previous 7 days. Subjects can answer the questionnaire with (1) very much, (2) a lot, (3) a little, or (4) not at all. The questionnaire is analyzed under 6 headings as follows: Symptoms and feelings (Questions 1 and 2); Daily activities (Questions 3 and 4); Leisure (Questions 5 and 6); Work and school (Question 7); Personal relations (Questions 8 and 9); and Treatment (Question 10).

In some embodiments, efficacy can be evaluated based upon improvement, PRO, in a subject's Hospital Anxiety and Depression Scale (HADS). In some embodiments, a JAK1 inhibitor, e.g., Compound 1, and/or methods of use described herein result in an improvement in a subject's response to HADS from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to HADS from baseline. HADS is 14-item questionnaire that assesses the levels of anxiety and depression that a person is currently experiencing. There are 7 questions each for measuring anxiety and for measuring depression, with 4 possible responses to each question (responses are scored as 0, 1, 2, or 3). Separate scores are calculated for anxiety and depression.

In some embodiments, efficacy can be evaluated based upon improvement, PRO, in a subject's WHO-5. In some embodiments, a JAK1 inhibitor, e.g., Compound 1, and/or methods of use described herein result in an improvement in a subject's response to WHO-5 from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to WHO-5 from baseline. The WHO-5 can be a validated, self-administered, 5-item questionnaire designed to assess mental well-being over the past 2 weeks, which can be used as an outcome measure for the wanted and unwanted effects of treatments. The questionnaire consists of 5 statements, which respondents rate according to the following scale: 0=At no time; 1=Some of the time; 2=Less than half of the time; 3=More than half of the time; 4=Most of the time; 5=All of the time.

The raw score is calculated by totaling the figures of the 5 answers for a range of 0 to 25, with 0 representing the worst possible and 25 representing the best possible quality of life. A score below 13 indicates poor well-being.

In some embodiments, efficacy can be evaluated based upon improvement in a subject's Treatment Satisfaction Questionnaire for Medication (TSQM). In some embodiments, a JAK1 inhibitor, e.g., Compound 1, and/or methods of use described herein result in an improvement in a subject's response to TSQM from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to TSQM from baseline. TSQM can be a validated 9-item questionnaire that measures a subject's satisfaction with treatment using a recall period of the past 2 to 3 weeks or since the treatment was last used. The questionnaire uses a 7-point scale for each question.

In some embodiments, efficacy can be evaluated based upon improvement in a subject's EQ-5D-5L questionnaire. In some embodiments, a JAK1 inhibitor, e.g., Compound 1, and/or methods of use described herein result in an improvement in a subject's response to the EQ-5D-5L questionnaire from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to EQ-5D-5L from baseline. The EQ-5D-5L questionnaire is a standardized, validated instrument for use as a measure of health outcome. The EQ-5D-5L questionnaire will provide data for use in economic models and analyses, including developing health utilities or Quality-Adjusted Life Years (QALYs). The EQ-5D-5L questionnaire consists of the following 2 sections: the EQ-5D descriptive system and the EQ VAS. The descriptive system comprises five dimensions: mobility, self-care, usual activities, pain/discomfort, and anxiety/depression.

Each dimension has 5 levels: Level 1 is "no problems," Level 2 is "slight problems," Level 3 is "moderate problems," Level 4 is "severe problems," and Level 5 is "extreme problems." This part of the EQ-5D-5L questionnaire provides a descriptive profile that can be used to generate a health state profile. For example, a subject in "health state 12345" would have no problems with mobility, slight problems with self-care (washing or dressing), moderate problems with doing usual activities, severe pain or discomfort and extreme anxiety or depression. Each health state can potentially be assigned a summary index score based on societal preference weights for the health state. These weights, sometimes referred to as utilities, are often used to compute QALYs for use in health economic analyses. Health state index scores generally range from less than 0 (where 0 is the value of a health state equivalent to dead; negative values representing values as worse than dead) to 1 (the value of full health), with higher scores indicating higher health utility. The health state preferences often represent national or regional values and can therefore differ between countries/regions. The EQ VAS records the subject's self-rated health on a vertical visual analogue scale (0 to 100), where the endpoints are labelled "the best health you can imagine" (100 score) and "the worst health you can imagine" (0 score).

The methods described herein utilize JAK1 pathway inhibitors, particularly JAK1 selective inhibitors. A JAK1 selective inhibitor is a compound that inhibits JAK1 activity preferentially over other Janus kinases. JAK1 plays a central role in a number of cytokine and growth factor signaling pathways that, when dysregulated, can result in or contribute to disease states. For example, levels of IL-6 (a pro-inflammatory cytokine) are elevated in subjects suffering from vitiligo (Singh, et al., Indian J Dermatology, 2012 January-February; 57(1): 12-14). In other autoimmune diseases and cancers, elevated systemic levels of inflammatory cytokines that activate JAK1 may also contribute to the disease and/or associated symptoms. Therefore, patients with autoimmune diseases like vitiligo may benefit from JAK1 inhibition. Selective inhibitors of JAK1 may be efficacious while avoiding unnecessary and potentially undesirable effects of inhibiting other JAK kinases.

In some embodiments, the JAK1 pathway inhibitor, or a pharmaceutically acceptable salt thereof, is selective for JAK1 over JAK2, JAK3, and TYK2 (i.e., a JAK1 selective inhibitor). For example, the compounds described herein, or pharmaceutically acceptable salts thereof, preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio>1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the JAK1 pathway inhibitor is a compound of Table 3, or a pharmaceutically acceptable salt thereof. The compounds in Table 3 are selective JAK1 inhibitors (selective over JAK2, JAK3, and TYK2). The $IC_{50}$ values obtained by the method of Example A at 1 mM ATP are shown in Table 3.

The compounds of Table 3 can be prepared by the synthetic procedures described, for example, in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

TABLE 3

| Comp. No. | Prep. | Name | Structure | JAK1 $IC_{50}$ (nM) | JAK2/ JAK1 |
|---|---|---|---|---|---|
| 1 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 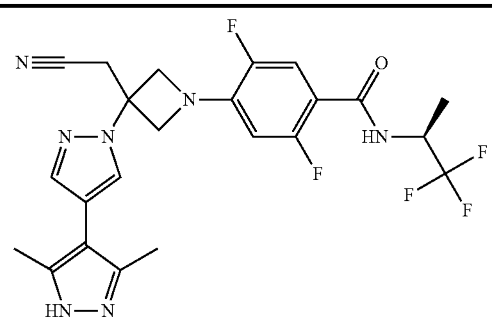 | +++ | >10 |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 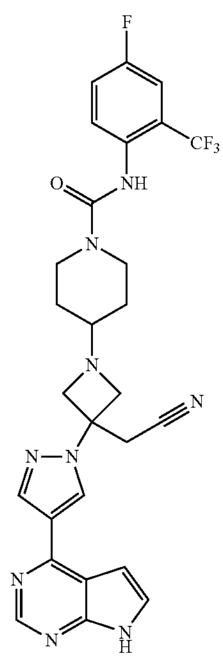 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 3-continued

| Comp. No. | Prep. | Name | Structure | JAK1 IC$_{50}$ (nM) | JAK2/JAK1 |
|---|---|---|---|---|---|
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 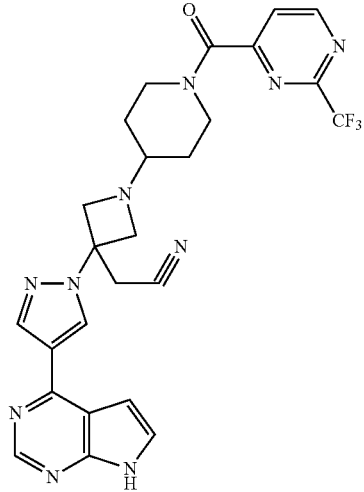 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2011/ 0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 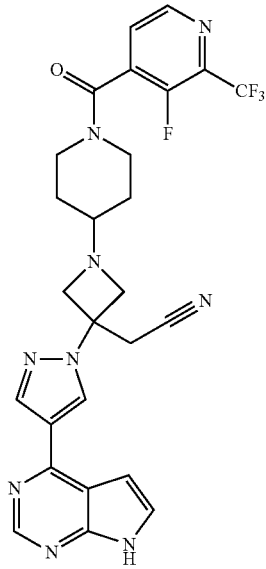 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 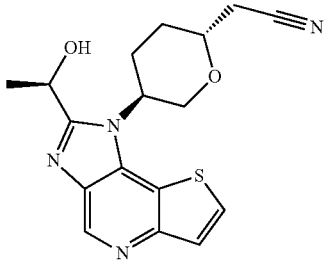 [SMILES: C[C@@H](O)c1nc2cnc3ccsc3c2n1[C@H]1CC[C@H](CC#N)OC1] | ++ | >10 |

TABLE 3-continued

| Comp. No. | Prep. | Name | Structure | JAK1 IC$_{50}$ (nM) | JAK2/ JAK1 |
|---|---|---|---|---|---|
| 6 | US 2010/ 0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 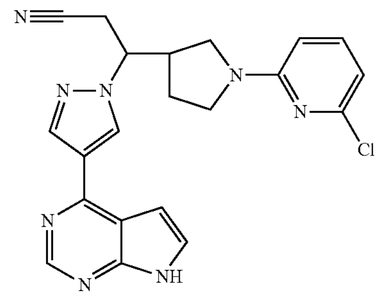 [SMILES: N#CCC(C1CCN(c2cccc(Cl)n2)C1)n1cc(-c2ncnc3[nH]ccc23)cn1] | + | >10 |
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 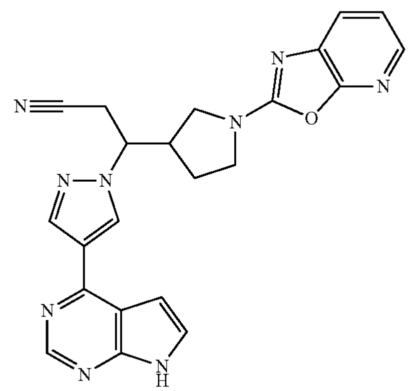 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 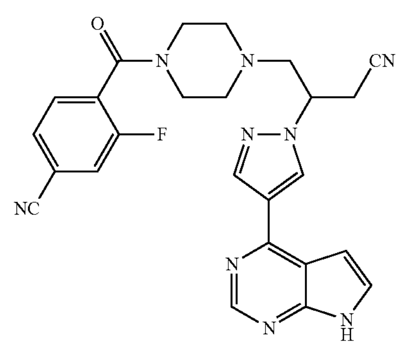 [SMILES: N#CCC(CN1CCN(C(=O)c2ccc(C#N)cc2F)CC1)n1cc(-c2ncnc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 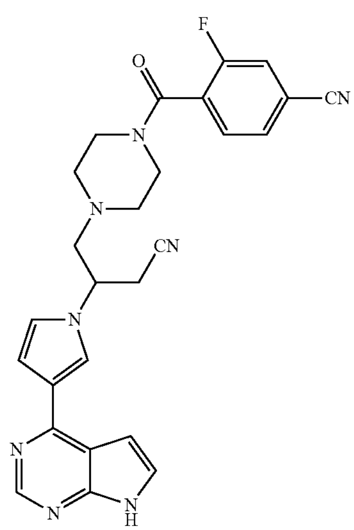 [SMILES: N#CCC(CN1CCN(C(=O)c2ccc(C#N)cc2F)CC1)n1ccc(-c2ncnc3[nH]ccc23)c1] | + | >10 |

TABLE 3-continued

| Comp. No. | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 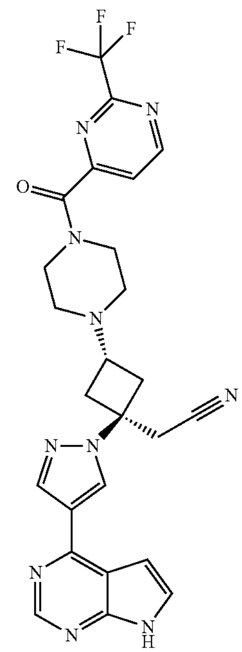 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 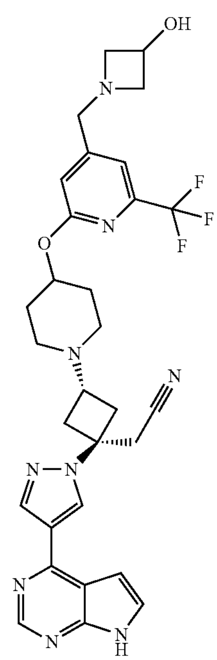 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 3-continued

| Comp. No. | Prep. | Name | Structure | JAK1 IC$_{50}$ (nM) | JAK2/ JAK1 |
|---|---|---|---|---|---|
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 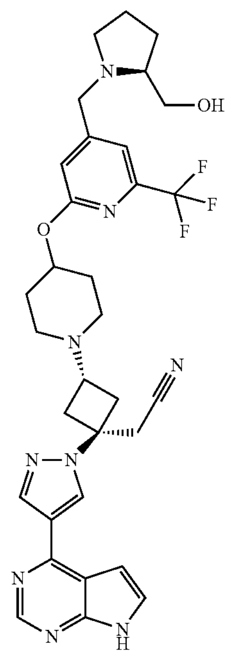 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 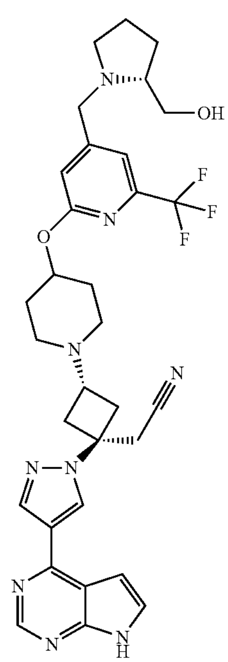 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE 3-continued

| Comp. No. | Prep. | Name | Structure | JAK1 IC$_{50}$ (nM) | JAK2/ JAK1 |
|---|---|---|---|---|---|
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 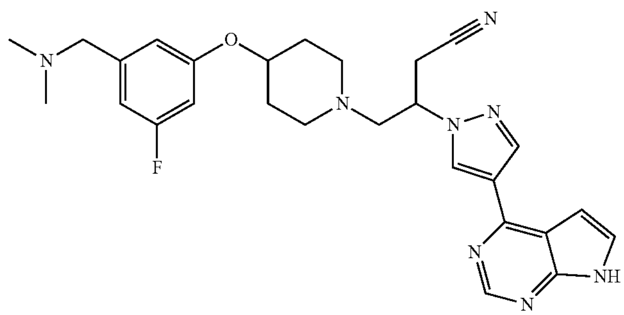 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 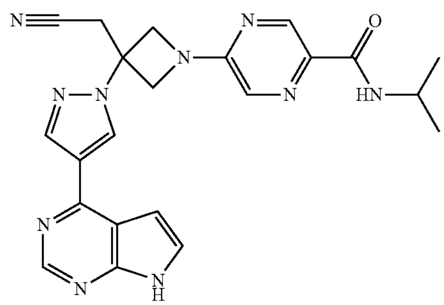 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 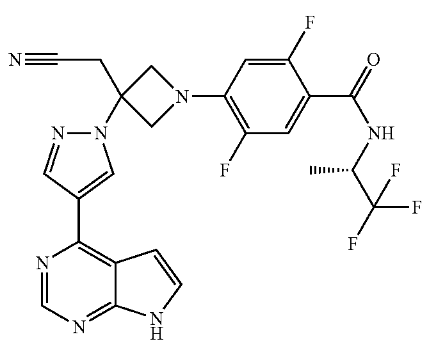 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 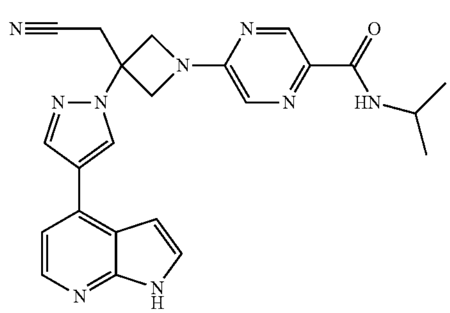 [SMILES: CC(C)NC(=O)c1cnc(N2CC(CC#N)(n3cc(-c4ccnc5[nH]ccc45)cn3)C2)cn1] | + | >10 |

TABLE 3-continued

| Comp. No. | Prep. | Name | Structure | JAK1 IC$_{50}$ (nM) | JAK2/ JAK1 |
|---|---|---|---|---|---|
| 18 | US 2013/ 0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 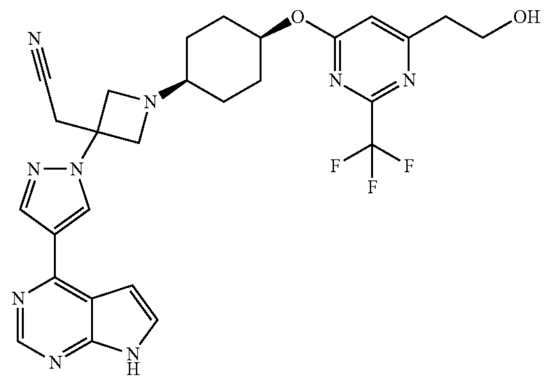 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/ 0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 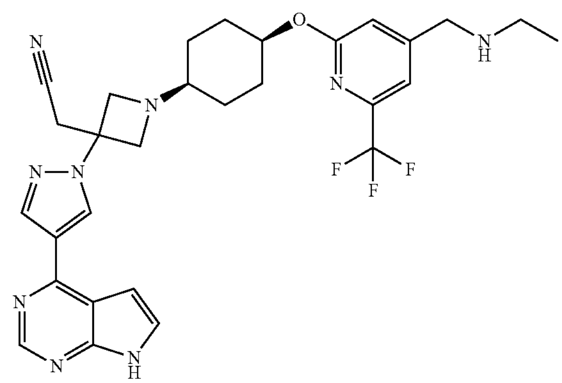 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 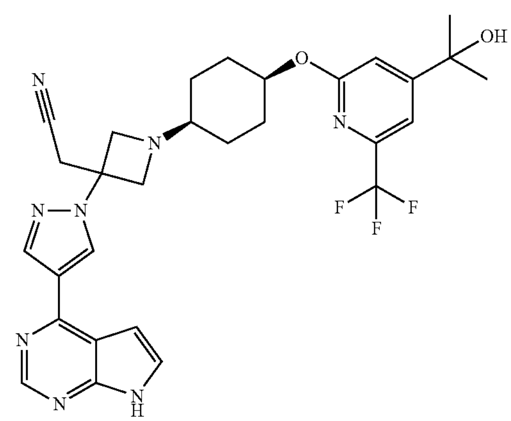 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 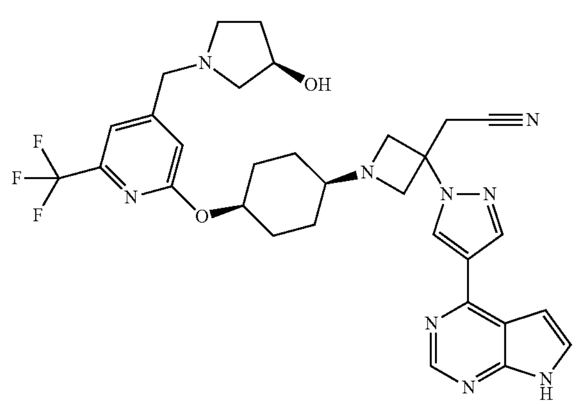 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |

TABLE 3-continued

| Comp. No. | Prep. | Name | Structure | JAK1 IC$_{50}$ (nM) | JAK2/ JAK1 |
|---|---|---|---|---|---|
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 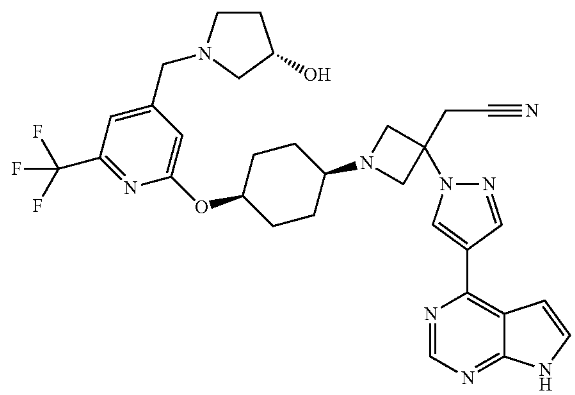 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 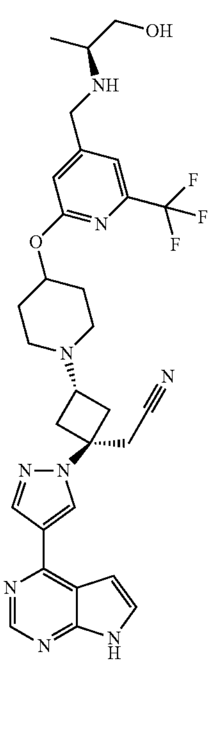 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 3-continued

| Comp. No. | Prep. | Name | Structure | JAK1 IC$_{50}$ (nM) | JAK2/ JAK1 |
|---|---|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 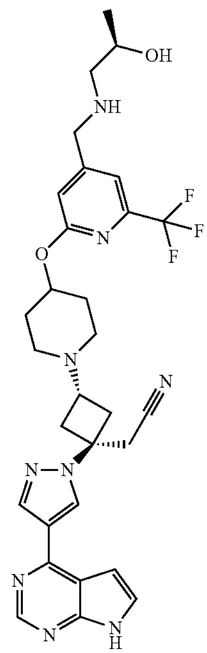 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 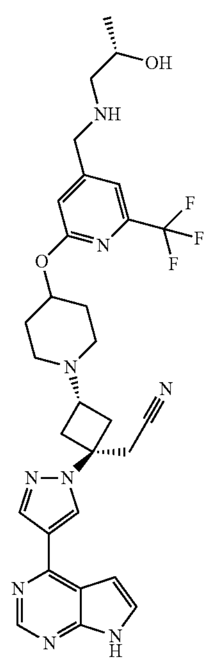 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 3-continued

| Comp. No. | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 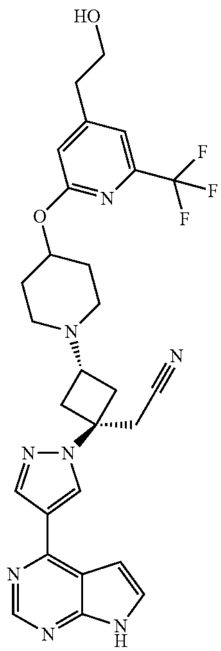 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)
++ means ≤100 nM (see Example A for assay conditions)
+++ means ≤300 nM (see Example A for assay conditions)
$^a$Data for enantiomer 1

$^b$Data for enantiomer 2

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (Compound 1), or a pharmaceutically acceptable salt thereof. In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt. Compound 1, and its salts, can be made by the procedures described in, e.g., U.S. Pat. No. 9,382,231 (see, e.g., Example 7), filed May 16, 2014, which is incorporated herein by reference in its entirety.

In some embodiments, the JAK1 pathway inhibitor is selected from the compounds, or pharmaceutically acceptable salts thereof, described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. No. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 pathway inhibitor is a compound of Formula I

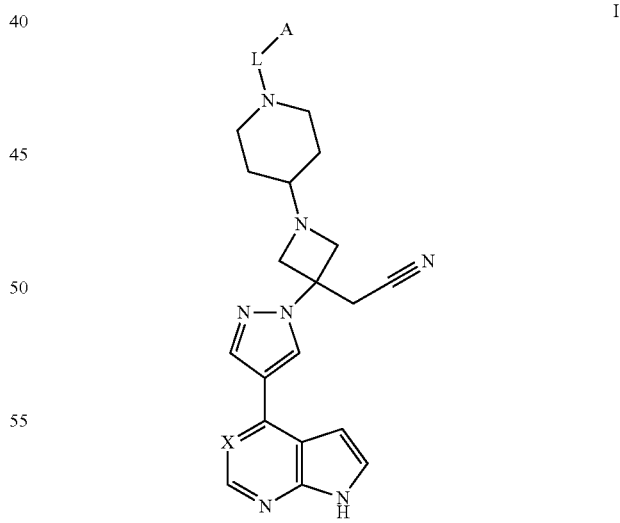

or a pharmaceutically acceptable salt thereof, wherein:
X is N or CH;
L is C(=O) or C(=O)NH;
A is phenyl, pyridinyl, or pyrimidinyl each of which is optionally substituted with 1 or 2 independently selected R$^1$ groups; and
each R$^1$ is, independently, fluoro, or trifluoromethyl.

In some embodiments, the compound of Formula I is {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl] carbonyl}piperidin-4-yl)azetidin-3-yl]acetonitrile, or a pharmaceutically acceptable salt thereof.

In some embodiments, the JAK1 pathway inhibitor is a compound of Formula II

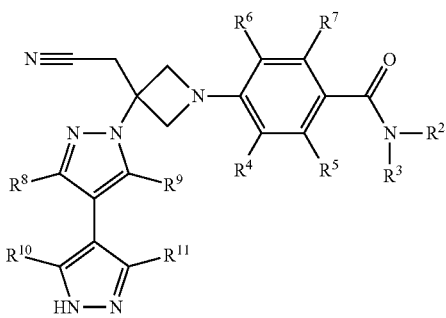

or a pharmaceutically acceptable salt thereof, wherein:
$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;
$R^3$ is H or methyl;
$R^4$ is H, F, or Cl;
$R^5$ is H or F;
$R^6$ is H or F;
$R^7$ is H or F;
$R^8$ is H or methyl;
$R^9$ is H or methyl;
$R^{10}$ is H or methyl; and
$R^{11}$ is H or methyl.

In some embodiments, the JAK1 pathway inhibitor is a compound of Formula III

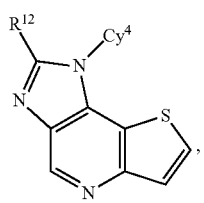

or a pharmaceutically acceptable salt thereof, wherein:
$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and
$R^{12}$ is —$CH_2$—OH, —CH($CH_3$)—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor, or a pharmaceutically acceptable salt thereof, is administered in a daily amount of from about 10 mg to about 100 mg on a free base basis. Accordingly, in some embodiments, the selective JAK1 pathway inhibitor is administered in a daily amount of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg on a free base basis. In some embodiments, the JAK1 pathway inhibitor, or a pharmaceutically acceptable salt thereof, is administered in a daily amount of from about 1 mg to about 100 mg on a free base basis. In some embodiments, the JAK1 pathway inhibitor, or a pharmaceutically acceptable salt thereof, is administered in a daily amount of from about 10 mg to about 80 mg on a free base basis. In some embodiments, the JAK1 pathway inhibitor, or a pharmaceutically acceptable salt thereof, is administered in a daily amount of about 90 mg on a free base basis. In some embodiments, the JAK1 pathway inhibitor, or a pharmaceutically acceptable salt thereof, is administered in a daily amount of about 75 mg on a free base basis. In some embodiments, the JAK1 pathway inhibitor, or a pharmaceutically acceptable salt thereof, is administered in a daily amount of about 45 mg on a free base basis. In some embodiments, the JAK1 pathway inhibitor, or a pharmaceutically acceptable salt thereof, is administered in a daily amount of about 15 mg on a free base basis.

The term "about" means "approximately" (e.g., plus or minus approximately 10% of the indicated value).

In some embodiments, the JAK1 pathway inhibitor, or a pharmaceutically acceptable salt thereof, is administered as one or more sustained release dosage forms each comprising the JAK1 pathway inhibitor, or a pharmaceutically acceptable salt thereof.

In some embodiments, the JAK1 pathway inhibitor, or a pharmaceutically acceptable salt thereof, is administered orally.

The embodiments described herein are intended to be combined in any suitable combination as if the embodiments are multiply dependent claims (e.g., the embodiments related to the selective JAK1 pathway inhibitor and doses of the same, the embodiments related to any salt forms of the compounds disclosed herein, the embodiments related to the individual types of cytokine related diseases or disorders, and the embodiments related to composition and/or administration can be combined in any combination).

All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, % $^{36}Cl$, $^{82}Br$, $^{75}Br$, $^{76}Br$, $^{77}Br$, $^{123}I$, $^{124}I$, $^{125}I$ and $^{131}I$ For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 3 can be optionally substituted with deuterium atoms, such as —$CD_3$ being substituted for —$CH_3$). The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

As used herein, the term "subject", "individual," or "patient," used interchangeably, refers to any animal, including mammals, preferably mice, rats, other rodents, rabbits, dogs, cats, swine, cattle, sheep, horses, or primates, and most preferably humans. In some embodiments, the "subject," "individual," or "patient" is in need of said treatment.

In some embodiments, the inhibitors are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the JAK1 inhibitors can prevent vitiligo in an individual who may be predisposed to the disease. The term "preventing" refers to blocking the occurrence of disease in a patient who may be predisposed to the disease but does not yet experience or display the pathology or symptomatology of the disease.

Combination Therapies

The methods described herein can further comprise administering one or more additional therapeutic agents. The one or more additional therapeutic agents can be administered to a patient simultaneously or sequentially. The one or more additional therapeutic agents can be administered using different methods than Compound 1 (e.g., topically).

In some embodiments, the additional therapeutic agent is selected from other JAK inhibitors. Additional JAK inhibitors may include ATI-50002 (JAK1/3 selective). Additional JAK inhibitors may include PF-06651600 (JAK3 selective). Additional JAK inhibitors may include PF06700841 (JAK1/TYK2 selective). Additional JAK inhibitors may include Upadacitinib. Additional JAK inhibitors may include Abrocitinib (JAK1 selective). Additional JAK inhibitors may include Cerdulatinib (JAK1/SYK selective). Additional JAK inhibitors may include Deucravacitinib (TYK2 selective).

In some embodiments, the additional therapeutic agent is selected from antioxidants. Antioxidants may be selected from pseudocatalase, vitamin E, vitamin C, ubiquinone, lipoic acid, Polypodium leucotomos, catalase/superoxide dismutase combination, and *Ginkgo biloba*. In some embodiments, antioxidants may be further administered in combination with phototherapy. The administration of antioxidants during or before phototherapy aims to counteract the oxidative stress induced by UV radiation itself, increasing the phototherapy effectiveness.

In some embodiments, the additional therapeutic agent is a wingless-related integration site (Wnt) agonist. Wnt agonists may include SKL2001.

In some embodiments, the additional therapeutic agent is a melanocortin 1 receptor (MC1R) agonist.

In some embodiments, the additional therapeutic agent is an inflammatory mediator. Inflammatory mediators may include Prostaglandin E2 (PGE2) and Bimatoprost (synthetic analog of prostaglandin F2a).

In some embodiments, the additional therapeutic agent is an antimetabolite. Antimetabolites may include 5-fluorouracil.

In some embodiments, the additional therapeutic agent includes Plasmid HSP70i gene therapy. Plasmid HSP70i gene therapy may include HSP70iQ435A.

In some embodiments, the additional therapeutic agent is selected from topical corticosteroids, immunomodulators, calcineurin inhibitors, and phototherapy. In some embodiments, the additional therapies are systemic steroids or immunosuppressants.

In some embodiments, the additional therapeutic agent includes steroids (e.g., orally administered steroids) including systemic steroids. Steroid treatment may include oral steroid minipulse therapy (e.g., using betamethasone and/or dexamethasone).

In some embodiments, topical corticosteroids are selected from augmented betamethasone dipropionate, clobetasol propionate, diflorasone diacetate, halobetasol propionate amcinonide, betamethasone valerate, desoximetasone, diflorasone diacetate, fluocinolone acetonide, halcinonide, and triamcinolone acetonide.

In some embodiments, the additional therapeutic agent includes immunomodulators. Immunomodulators may include PDE4 inhibitors (e.g., apremilast (e.g., orally) or crisaborole (e.g., topically)). Immunomodulators may include anti-CD20 therapy (e.g., ofatumumab). Immunomodulators may include anti-CD19 therapy (e.g., tafasitamab). Immunomodulators may include anti-IL15 therapy (e.g., AMG 714 monoclonal antibody). Immunomodulators may include anti-IL36 therapy (e.g., imsidolimab and spesolimab). Immunomodulators may include anti-TNFalpha therapy (e.g., etanercept and infliximab). Immunomodulators may include anti-CD122 therapy.

In some embodiments, immunomodulators are selected from apremilast, crisaborole, afamelanotide, rituximab, ofatumumab, tafasitamab, minocycline, latanoprost, zinc, tofacitinib, AMG 714 monoclonal antibodies, imsidolimab, spesolimabcyclosporine, etanercept, infliximab, cyclophosphamide, ciclosporin, methotrexate, and sodium oxo-dihydro-acridinylacetate (ODHAA).

In some embodiments, calcineurin inhibitors are selected from tacrolimus (FK-506) and pimecrolimus.

In some embodiments, phototherapy includes exposure to ultraviolet (e.g., excimer lamps or lasers).

In some embodiments, the additional therapeutic agent is a Janus kinase inhibitor. In some embodiments, the Janus kinase inhibitor is ruxolitinib, or a pharmaceutically acceptable salt thereof. In some embodiments, the ruxolitinib is administered topically. The topical administration of ruxolitinib is described in greater detail, for example, in US Patent Publ. No. 2011/0288107, filed Mar. 20, 2011, and Persaud et al., "Plasma pharmacokinetics and distribution of ruxolitinib into skin following oral and topical administration in minipigs" Int J Pharm, 590:119889, Nov. 30, 2020, PMID: 32949620, which are incorporated herein by reference in their entirety.

In some embodiments, the additional therapeutic agent is an IL-6 antagonist or receptor antagonist. In some embodiments, the IL-6 receptor antagonist is tocilizumab.

In some embodiment, the methods described herein can further comprise the use in combination with surgical techniques. In some embodiments, surgical techniques include surgical skin grafts.

Pharmaceutical Formulations and Dosage Forms

When employed as pharmaceuticals, the JAK1 pathway inhibitors or pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, foams, liquids and powders. Conventional pharmaceutical carriers, aqueous, powder or oily bases, thickeners and the like may be necessary or desirable.

This invention also includes pharmaceutical compositions which contain, as the active ingredient, the JAK1 pathway inhibitor described herein, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The JAK1 pathway inhibitors may be milled using known milling procedures such as wet milling to obtain a particle size appropriate for tablet formation and for other formulation types. Finely divided (nanoparticulate) preparations of the JAK1 selective inhibitors can be prepared by processes known in the art, e.g., see International App. No. WO 2002/000196.

The compositions can be formulated in a unit dosage form, each dosage containing a set amount of the active ingredient as the free form or a salt form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Kits

The present invention also includes pharmaceutical kits useful, for example, in the treatment and/or prevention of vitiligo, which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

Example A: In Vitro JAK Kinase Assay

JAK1 pathway inhibitors that can be used for the treatment of cytokine-related diseases or disorders were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, MA). Binding to the Europium labeled antibody took place for 40 minutes and HTRF signal was measured on a Fusion plate reader (Perkin Elmer, Boston, MA). The compounds in Table 3 were tested in this assay and shown to have the $IC_{50}$ values also found in Table 3.

Example B: In Vitro JAK Kinase Assay Using Melanocyte Proliferation Assay with 20% CD8+ T Cell Conditioned Media The assay investigates an in vitro system using CD8+ T Cells and melanocytes. The assay tests whether Compound 1 modulates the inflammatory response and how such modulation affects melanocyte biology.

Methods: CD8+ T cell Conditioned Media Step: Normal Human CD8+ T Cells from peripheral blood were purchased (STEMCELL Technologies). They were cultured for 48 hours at 37 C and 5% $CO_2$ under activating and unactivating conditions inside the Incucyte Live-Cell Analysis System (Essen Bioscience). Activated T cells were cultured in a flat bottom 96 well plate (Costar) that was first coated with 10 ug/ml anti-CD3 (BD Biosciences) for 2 hours at room temperature and then washed one time with PBS before cells were added. They were grown in Melanocyte Growth Medium (NHM-GM, MatTek) containing 1 ug/ml anti-CD28 (BD Biosciences). Unactivated T cells were treated the same way except that they were cultured in a separate plate without anti-CD3 and anti-CD28. Each T cell plate was treated at seeding with Compound 1 (1000, 100, or 10 nM) or media alone. Each treatment was done in triplicate. After 48 hours, all the samples (T cells and media) were transferred to new V-bottom plates and centrifuged at 1300 RPMs for 10 minutes. Supernatants were collected from the T cell pellets carefully to not disturb the pellet. The supernatants (CD8+ T cell Conditioned Media) used fresh to treat the melanocyte. The remaining amounts were stored at −80 C and then thawed for protein analysis by Luminex technology (custom Procarta 45-plex, Thermo Fisher Scientific). The treated CD8+ T cell pellets were lysed using the Quantigene sample processing kit reagents following the kit instructions. Lysates were stored at −80 C and then thawed for RNA analysis by Luminex technology using two custom Quantigene 80-Plexes—150 targeted genes total (Thermo Fisher Scientific).

Melanocyte Proliferation Step: Normal Human Melanocytes isolated from a black donor's neonatal foreskin epidermis were purchased (MatTek). They were thawed and seeded following manufacturer's instruction in NHM-GM media in flat bottom 96 well plates (Costar) for 18 hours at 37 C and 5% $CO_2$. They were approximately 10% confluent when treated with 20% CD8+ T cell Conditioned Media (25 ul Conditioned media added to 100 ul of NHM-GM already in the wells). They were cultured for 48 hours at 37 C and 5% $CO_2$ inside the Incucyte Live-Cell Analysis System (Essen Bioscience) with 5 images per well taken every 3 hrs. After 48 hours, all the supernatants were transferred from the melanocyte plates to new V-bottom plates and centrifuged at 1300 RPMs for 10 minutes. Supernatants were collected and were stored at −80 C and then thawed for protein analysis by Luminex technology (custom Procarta 45-plex, Thermo Fisher Scientific). The treated melanocytes were lysed using the Quantigene sample processing kit reagents following the kit instructions. Lysates were stored at −80 C and then thawed for RNA analysis by Luminex technology using two custom Quantigene 80-Plexes for a total of 150 targeted genes (Thermo Fisher Scientific). Incucyte images were analyzed using the Incucyte software and the percentage of melanocyte confluence was determined for each treatment.

Figure 1:
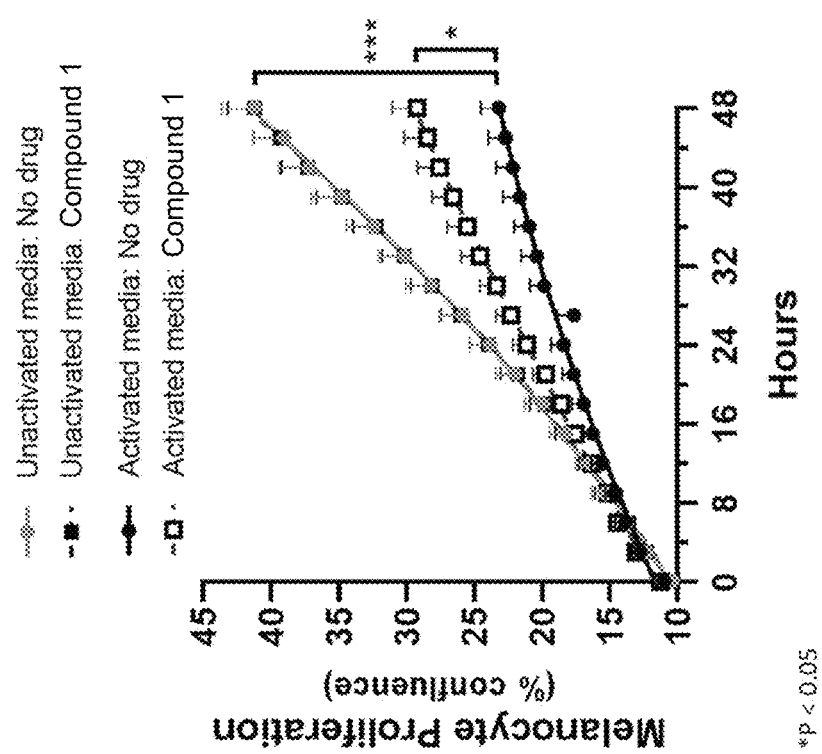
FIG. 1 is a graph depicting melanocyte proliferation, % confluence vs. time (hours).

Results: FIG. 1 is a graph depicting melanocyte proliferation, % confluence vs. time (hours). Compound 1 does not directly alter melanocyte proliferation following transfer of 20% unactivated T cell media. Addition of 20% media from CD3/CD28-activated human CD8+ T cells to the NHM-GM in vitro culture significantly inhibited melanocyte proliferation compared to unactivated conditions. Compound 1 (1000 nM) co-cultured with the CD3/CD28-activated human CD8+ T cells partially reversed the suppressed melanocyte proliferation response. This improvement of melanocyte proliferation was statistically significant. Compound 1 added to the inflammatory culture media results in a significant reduction of spontaneous proliferation compared to the natural melanocyte proliferation rate. It is a time-dependent reduction of the spontaneous natural proliferation response.

FIG. 2 is a graph depicting the effect of Compound 1 on JAK1-dependent cytokines using T-cell compartments, protein T cell media (pg/ml) vs. specific JAK1-dependent cytokines. Consistent with previously reported data Compound 1 co-cultured with the CD3/CD28-activated human CD8+ T cells inhibits inflammatory cytokines that are JAK-STAT dependent.

FIGS. 3A-C are graphs depicting the effect of Compound 1 on growth factors and chemokine using T-cell compartments, protein T cell media (pg/ml) vs. IL-8 (A), HGF (B), and LIF (C). Compound 1 co-cultured with the CD3/CD28-activated human CD8+ T cells reduced several additional mediators that are not obligated to use JAK1 signaling.

Figures 5A, 5B, 5C:
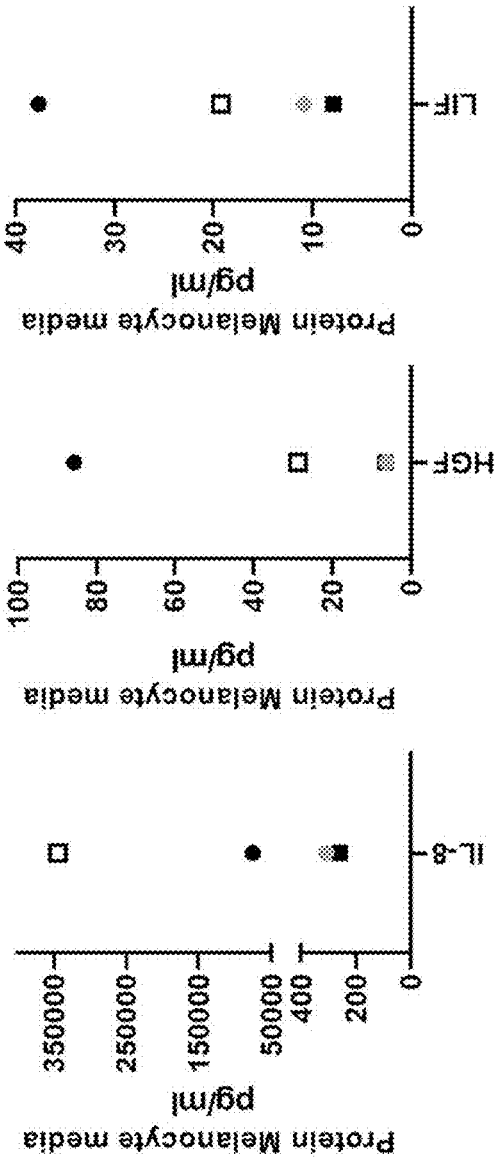
FIGS. 5A-C are graphs depicting the effect of Compound 1 on growth factors and chemokine using melanocytes, protein melanocyte media (pg/ml) vs. IL-8 (A), HGF (B), and LIF (C).

FIG. 4 is a graph depicting the effect of Compound 1 on JAK1-dependent cytokines using melanocytes, protein melanocyte media (pg/ml) vs. specific JAK1-dependent cytokines. Compound 1 reduces inflammatory cytokines that are JAK-STAT dependent. Several of these cytokines are upregulated by melanocytes under stress conditions (IFNγ, CXCL10, IL-6). FIGS. 5A-C are graphs depicting the effect of Compound 1 on growth factors and chemokine using melanocytes, protein melanocyte media (pg/ml) vs. IL-8 (A), HGF (B), and LIF (C). IL-8 is upregulated by melanocytes under stress conditions and this is increased in Compound 1 conditions.

Discussion: Hepatocyte Growth Factor (HGF)/mesenchymal-epithelial transition factor (c-MET) signaling protects melanocytes from apoptosis and stimulates their proliferation and motility. HCF concentrations increased in melanocyte culture supernatants following transfer of activated T cell conditioned media. Compound 1 significantly reduced HGF levels (~67%) but melanocyte proliferation was increased. Based on the data (melanocytes and T cells), reduction of HGF expression by Compound 1, via a signaling mechanism, would be expected to be detrimental on melanocyte proliferation.

Interleukin-8 (IL-8/CXCL8) is reported to potentiate the proliferative response of melanocytes to multiple growth factors via binding to its cognate receptors (CXCR1 & CXCR2). IL-8 production and CXCR1/2 signaling are both JAK1 independent. Compound 1 treatment of CD8+ T cells slightly reduced IL-8 concentration (1,22%) however there was a profound increase (↓~450%) in the melanocyte culture. Based on the data (melanocytes and T cells), unexpected upregulation of IL-8 levels in melanocyte cultures was observed that would enhance proliferative response.

Leukemia inhibitory factor (LIF) increases primary melanocyte proliferation and differentiation. LIF receptor signaling is JAK1-dependent and therefore Compound 1 would be expected to have a detrimental affect on melanocyte proliferation. Unexpectedly, melanocyte proliferation is increased. Based on the data (T cells), on-target inhibition of LIF is not matched by enhanced melanocyte proliferation response.

Compound 1 can downregulate inflammatory cytokines in a CD8+ activated T cell microenvironment. It allows melanocyte proliferation to normalize and also stops the generation of inflammatory mediators from the melanocyte.

Example C: Phase 2 Study of Compound 1

Study Design

Figure 6:
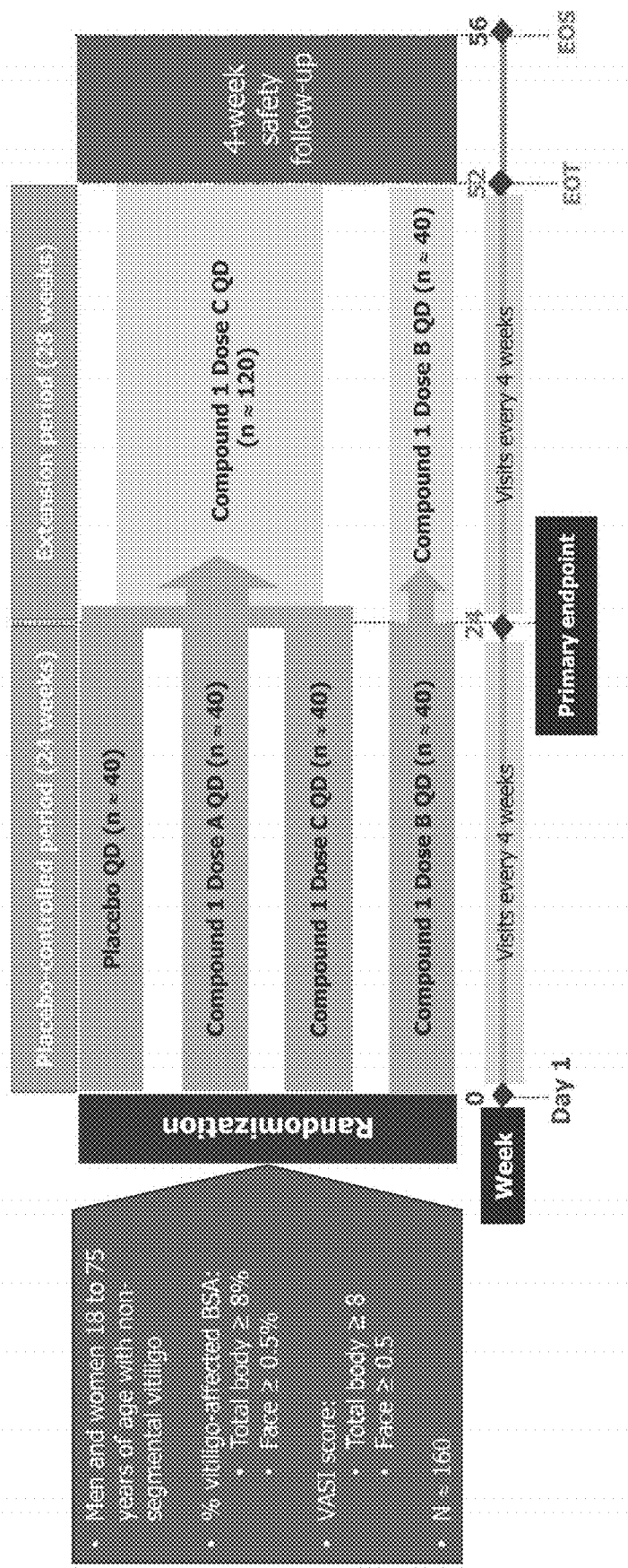
FIG. 6 depicts an outline of a phase 2 randomized, double-blind, placebo-controlled dose-ranging study of the efficacy and safety of Compound 1.

FIG. 6 depicts an outline of a phase 2 randomized, double-blind, placebo-controlled dose-ranging study of the efficacy and safety of Compound 1. A study is conducted using Compound 1 for treating participants with non-segmental vitiligo. The study can include a 28-week double-blind extension period in participants with vitiligo. Participants can include those with non-segmental vitiligo who have depigmented areas ≥8% total BSA, ≥8 T-VASI, ≥0.5% BSA on the face, and ≥0.5 F-VASI. Participants will be stratified based on total BSA involvement (8-20% and >20%). In some embodiments, participants can include those with non-segmental vitiligo who have depigmented areas ≥5% total BSA including ≥5 T-VASI, ≥0.5% BSA on the face and ≥0.5 F-VASI. Participants will be stratified based on total BSA involvement (8-20% and >20%). The study can include men and women aged 18 to 75 years of age.

The 24-week placebo-controlled double-blind period will randomize approximately 160 participants 1:1:1:1 to 1 of 3 treatment groups (Dose A, Dose B, or Dose C) or the placebo group. The 28-week double-blind extension will include all participants who successfully complete the placebo-controlled period. In some embodiments, the JAK1 pathway inhibitor, or a pharmaceutically acceptable salt thereof, will be administered in a daily amount of about Dose B on a free base basis. In some embodiments, the JAK1 pathway inhibitor, or a pharmaceutically acceptable salt thereof, will be administered in a daily amount of about Dose C on a free base basis. The primary endpoint is the Percent change from baseline in Total Vitiligo Area Scoring Index (T-VASI) at Week 24, and the key secondary endpoint is the proportion of participants achieving T-VASI50 at Week 24. In some embodiments, the outcome of this study will be instrumental in informing dose selection to be evaluated in a Phase 3 study.

In some embodiments, criteria for participants to be excluded from the study include any one of the following: other skin depigmentation disorders (e.g., piebaldism, *pityriasis* alba, leprosy, postinflammatory hypopigmentation, progressive macule hypomelanosis, nevus anemicus, chemical leukoderma, and tinea *versicolor*); uncontrolled thyroid function at screening as determined by the investigator (Note: If the participant has a history of thyroid disease and is on treatment, the participant must be on a stable thyroid regimen for at least three months prior to Day 1); use of laser or light-based treatment (phototherapy), including tanning beds within 8 weeks prior to Day 1; use of dihydroxyacetone (generally present in self-tanning products) within 4 weeks prior to Day 1; current or past use of the depigmenting agent monobenzyl ether of hydroquinone, including Benoquin® (monobenzone); history of melanocyte-keratinocyte transplantation procedure (MKTP) or other surgical treatment for vitiligo; spontaneous and significant repigmentation within 6 months prior to screening (eg, repigmentation without any treatment, and significant in amount as determined by the investigator); women who are pregnant or who are considering pregnancy, or breastfeeding; history of treatment failure to vitiligo, or any other inflammatory condition, with any systemic or topical JAK or TYK2 inhibitor (e.g., ruxolitinib, tofacitinib, baricitinib, filgotinib, lestaurtinib, pacritinib, abrocitinib, brepocitinib); current use of anticoagulants or medications known to cause thrombocytopenia; hepatitis: evidence of HBV or HCV infection or risk of reactivation (participant cannot be positive for HBV DNA, HCV RNA, HBsAg, or anti-hepatitis B core antibody; however, participants with no prior history of HBV infection who have been vaccinated against HBV and who have a positive antibody against HBV surface antigen (anti-HBs+) as the only evidence of prior exposure may participate in the study); known HIV infection; known hypersensitivity or severe reaction to Compound 1 or excipients of Compound 1; inability or unlikeliness of the participant to comply with the dose schedule and study evaluations, in the opinion of the investigator; and any condition that would, in the investigator's judgment, interfere with full participation in the study, including administration of study drug and attending required study visits; pose a significant risk to the participant; or interfere with interpretation of study data.

In some embodiments, criteria for participants to be excluded from the study include participants with concurrent conditions or history of other diseases, including any one of the following: thrombocytopenia, coagulopathy, platelet dysfunction, or history of thrombotic events; any clinically significant medical condition other than vitiligo, as determined by the investigator, that is not adequately controlled with appropriate treatment or may interfere with the course, severity, or assessments of this study; any other active skin disease or condition that may interfere with the course, severity, or assessments of this study; any bacterial, fungal, or viral infection, based on the investigator's clinical assessment, make the participant an unsuitable candidate for the study; current herpes zoster infection, a history of disseminated herpes simplex, or a history of herpes zoster; history of malignancy, including melanoma, lymphoma and leukemia within 5 years before Day 1, other than a successfully treated nonmetastatic cutaneous squamous cell carcinoma, basal cell carcinoma, or localized carcinoma in situ of the cervix; and albinism.

In some embodiments, criteria for participants to be excluded from the study include receipt of medications or investigational drugs within the following interval before Day 1 (first administration of study drug): <12 weeks or 5 half-lives (if known), whichever is longer, for any topical or systemic JAK or TYK2 inhibitor; <12 weeks or 5 half-lives (if known), whichever is longer, for any investigational or experimental treatments; <12 weeks or 5 half-lives (if known), whichever is longer, for systemic immunosuppressive or immunomodulating biologic drugs (eg, egadalimumab, etanercept, infliximab, golimumab, certolizumab, ustekinumab, secukinumab, brodalumab, ixekizumab, risankizumab, guselkumab, bimekizumab, iscalimab, bermekimab, rituximab, anakinra); <6 weeks for live vaccine, or planning to receive live vaccine during the course of the study or within 6 weeks after the last dose of study drug; <4 weeks for systemic immunosuppressive or immunomodulating small molecule drugs (e.g., oral or injectable corticosteroids, methotrexate, cyclosporine, dapsone, azathioprine); <3 weeks for any oral or topical PDE-4 inhibitor (eg, apremilast, crisaborole); <2 weeks for any topical drug applied onto vitiligo lesions; <2 weeks for any OTC therapies used for vitiligo treatment; <2 weeks or 5 half-lives (if known), whichever is longer, for strong and moderate systemic CYP3A4 inhibitors and strong systemic CYP3A4 inducers within 2 weeks or 5 half-lives (if known). Examples include but are not limited to the following medications: erythromycin, rifampicin/rifampin, ciprofloxacin, some azole antifungals (eg, ketoconazole, fluconazole), nefazodone, St. John's Wort, diltiazem, mibefradil, verapamil, grapefruit/grapefruit juice, and Seville oranges; and <1 week for anti-platelet.

In some embodiments, criteria for participants to be excluded from the study include use of systemic immunosuppressive or immunomodulating small molecule drugs note: that use of corticosteroid inhalers and intranasal sprays is allowed; use of oral corticosteroids for nondermatologic conditions (e.g., asthma exacerbation, bronchitis) is allowed for no longer than 7 days, if deemed acceptable by the investigator and the sponsor; and use of topical corticosteroids for dermatologic disease besides vitiligo (e.g., atopic dermatitis or psoriasis) is allowed for areas not being treated for vitiligo (the total BSA involvement for other dermatologic diseases, outside of the areas treated for vitiligo, must not exceed 10%).

In some embodiments, criteria for participants to be excluded from the study include use of systemic immunosuppressive or immunomodulating small molecule drugs note low dose acetyl salicylic acid (≤100 mg QD) is permitted for the purpose of cardiovascular prophylaxis at the discretion of the investigator.

In some embodiments, criteria for participants to be excluded from the study include evidence of active or latent or inadequately treated infection with *Mycobacterium tuberculosis* (i.e., TB) as defined by at least one of the following: a positive QuantiFERON®-TB Gold In-Tube test (QFT-GIT) or positive Mantoux/PPD tuberculin skin test performed at or within the 12 weeks prior to Day 1 is exclusionary and a negative test is required for eligibility, unless other criteria as described here are applicable (note it is recommended that participants with a history of Bacille Calmette Guerin vaccination be tested with the QFT-GIT, since the Mantoux/PPD tuberculin skin test may be positive due to vaccination (note a QFT-GIT or Mantoux/PPD tuberculin skin test is not required if the participant has previously received a documented adequate course of therapy for either latent or active TB infection)); a history of either untreated or inadequately treated latent or active TB infection; if a participant has previously received an adequate course of therapy for either latent (9 months of isoniazid in a locale where rates of primary multidrug TB resistance are <5% or an acceptable alternative regimen) or active (acceptable multidrug regimen) TB infection, neither a QFT-GIT nor a Mantoux/PPD tuberculin skin test is needed, but a chest radiograph(s) or other appropriate diagnostic image, performed within 3 months of Day 1, is required (note to be considered eligible for the study, the radiograph(s) must be negative for active tuberculosis infection as determined by a qualified radiologist and documentation of adequate treatment for TB and negative chest radiograph(s) results must be obtained prior to Day 1; and a participant who is currently being treated for active TB infection.

In some embodiments, criteria for participants to be excluded from the study include participants with laboratory values at screening defined in Table 4:

TABLE 4

| | Laboratory Parameter | Exclusion Criterion |
|---|---|---|
| | Hematology | |
| a | Platelets | $<150 \times 10^9$/L |
| b | Hemoglobin | $<10$ g/L |
| c | ANC | $<1.5 \times 10^9$/L |
| d | WBCs | $\leq 3.0 \times 10^9$/L |
| | Hepatic | |
| e | ALT | $\geq 2 \times$ ULN |
| f | AST | $\geq 2 \times$ ULN |
| g | Total bilirubin | $\geq 1.5 \times$ ULN (Note: unless clinical diagnosis of Gilbert's syndrome) |
| h | Alkaline phosphatase | $\geq 2 \times$ ULN |
| | Renal | |
| j | Serum creatinine | $>1.25 \times$ ULN |
| | Coagulation | |
| l | PT (and calculated INR) | >ULN |
| m | INR | >ULN |

Example D: In Vitro JAK Kinase Assay Using Melanocyte Proliferation Assay with 20% CD8+ T Cell Conditioned Media The assay investigates an in vitro system using CD8+ T Cells and melanocytes. The assay tests whether ruxolitinib modulates the inflammatory response and how such modulation affects melanocyte biology.

Methods: CD8+ T cell Conditioned Media Step: Normal Human CD8+ T Cells from peripheral blood were purchased (STEMCELL Technologies). They were cultured for 48 hours at 37 C and 5% $CO_2$ under activating and unactivating conditions inside the Incucyte Live-Cell Analysis System (Essen Bioscience). Activated T cells were cultured in a flat bottom 96 well plate (Costar) that was first coated with 10 ug/ml anti-CD3 (BD Biosciences) for 2 hours at room temperature and then washed one time with PBS before cells were added. They were grown in Melanocyte Growth Medium (NHM-GM, MatTek) containing 1 ug/ml anti-CD28 (BD Biosciences). Unactivated T cells were treated the same way except that they were cultured in a separate plate without anti-CD3 and anti-CD28. Each T cell plate was treated at seeding with ruxolitinib (1000, 100, or 10 nM) or media alone. Each treatment was done in triplicate. After 48 hours, all the samples (T cells and media) were transferred to new V-bottom plates and centrifuged at 1300 RPMs for 10 minutes. Supernatants were collected from the T cell pellets carefully to not disturb the pellet. The supernatants (CD8+ T cell Conditioned Media) used fresh to treat the melanocyte. The remaining amounts were stored at −80 C and then thawed for protein analysis by Luminex technology (custom Procarta 45-plex, Thermo Fisher Scientific). The treated CD8+ T cell pellets were lysed using the Quantigene sample processing kit reagents following the kit instructions. Lysates were stored at −80 C and then thawed for RNA analysis by Luminex technology using two custom Quantigene 80-Plexes—150 targeted genes total (Thermo Fisher Scientific).

Melanocyte Proliferation Step: Normal Human Melanocytes isolated from a black donor's neonatal foreskin epidermis were purchased (MatTek). They were thawed and seeded following manufacturer's instruction in NHM-GM media in flat bottom 96 well plates (Costar) for 18 hours at 37 C and 5% $CO_2$. They were approximately 10% confluent when treated with 20% CD8+ T cell Conditioned Media (25 ul Conditioned media added to 100 ul of NHM-GM already in the wells). They were cultured for 48 hours at 37 C and 5% $CO_2$ inside the Incucyte Live-Cell Analysis System (Essen Bioscience) with 5 images per well taken every 3 hrs. After 48 hours, all the supernatants were transferred from the melanocyte plates to new V-bottom plates and centrifuged at 1300 RPMs for 10 minutes. Supernatants were collected and were stored at −80 C and then thawed for protein analysis by Luminex technology (custom Procarta 45-plex, Thermo Fisher Scientific). The treated melanocytes were lysed using the Quantigene sample processing kit reagents following the kit instructions. Lysates were stored at −80 C and then thawed for RNA analysis by Luminex technology using two custom Quantigene 80-Plexes for a total of 150 targeted genes (Thermo Fisher Scientific). Incucyte images were analyzed using the Incucyte software and the percentage of melanocyte confluence was determined for each treatment.

Figure 7:
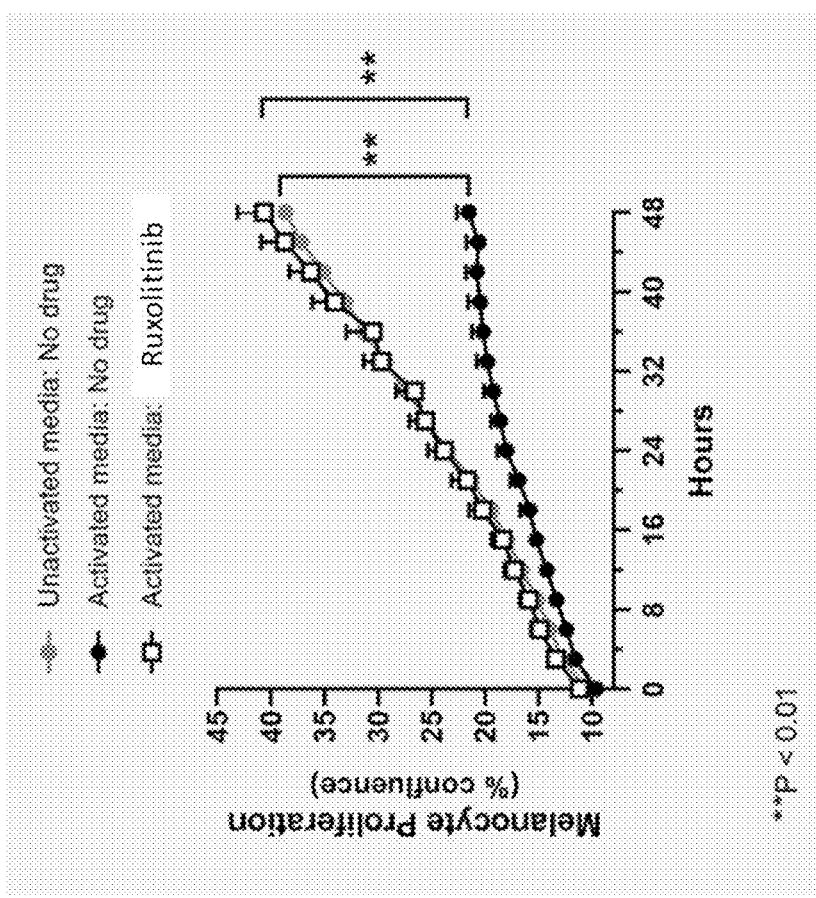
FIG. 7 is a graph depicting melanocyte proliferation, % confluence vs. time (hours).

Results: FIG. 7 is a graph depicting melanocyte proliferation, % confluence vs. time (hours). Addition of 20% media from CD3/CD28-activated human CD8+ T cells to the NHM-GM in vitro culture significantly inhibited melanocyte proliferation compared to unactivated conditions. Ruxolitinib (1000 nM) co-cultured with the CD3/CD28-activated human CD8+ T cells appeared to completely reverse the suppressed melanocyte proliferation response. This improvement of melanocyte proliferation was statistically significant. Ruxolitinib added to the inflammatory culture media results in a significant reduction of spontaneous proliferation compared to the natural melanocyte proliferation rate. It is a time-dependent reduction of the spontaneous natural proliferation response.

Figure 8:
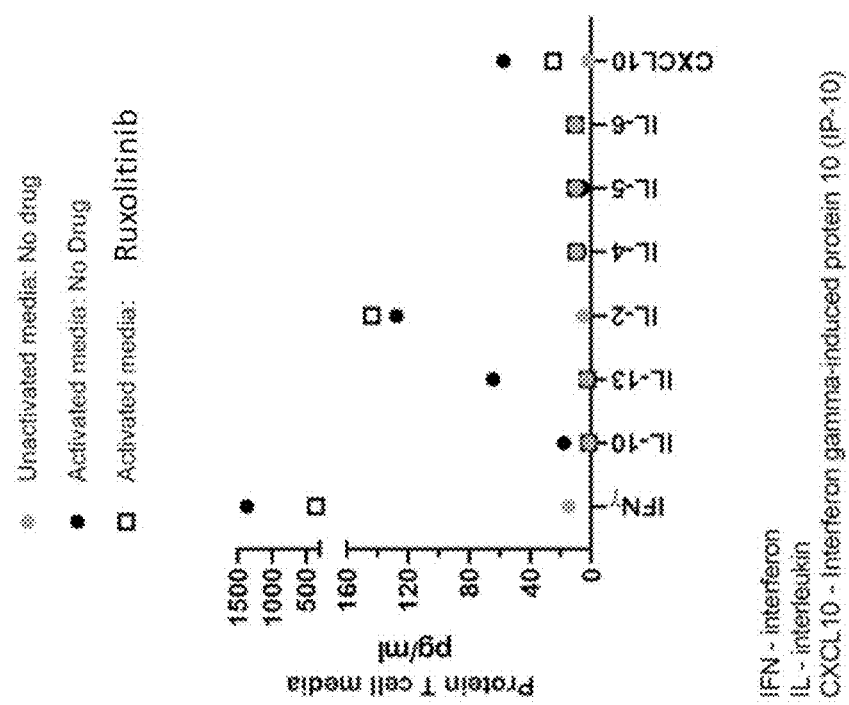
FIG. 8 is a graph depicting the effect of ruxolitinib on JAK1-dependent cytokines using T-cell compartments, protein T cell media (pg/ml) vs. specific JAK1-dependent cytokines.

FIG. 8 is a graph depicting the effect of ruxolitinib on JAK1-dependent cytokines using T-cell compartments, protein T cell media (pg/ml) vs. specific JAK1-dependent cytokines. Consistent with previously reported data ruxolitinib co-cultured with the CD3/CD28-activated human CD8+ T cells inhibits inflammatory cytokines that are JAK-STAT dependent except for inflammatory cytokine IL-2 which is upregulated (there appears to be no effect for inflammatory cytokines IL-4, IL-5 (it is noted that IL-5 is JAK2/2), and IL-6).

Figure 9B:
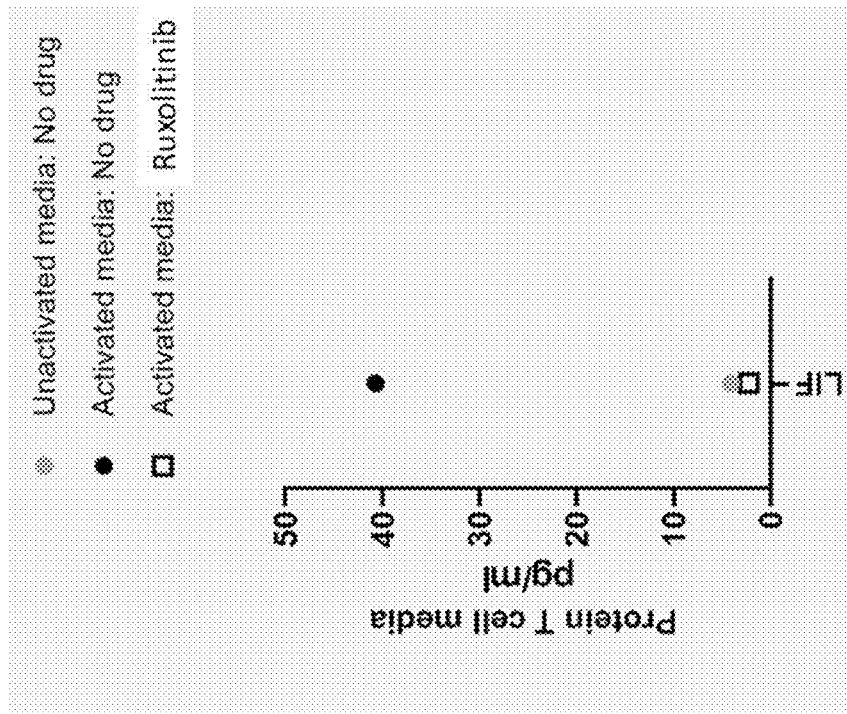
FIGS. 9A-B are graphs depicting the effect of ruxolitinib on growth factors and chemokine using T-cell compartments, protein T cell media (pg/ml) vs. IL-8 (A) and LIF (B).
Figure 9A:
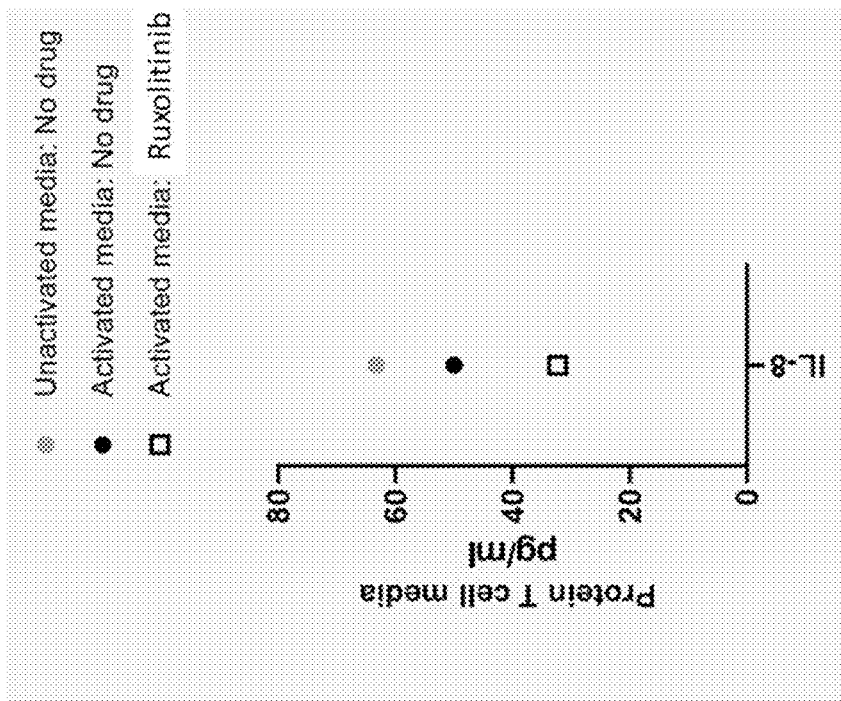

FIGS. 9A-B are graphs depicting the effect of ruxolitinib on growth factors and chemokine using T-cell compartments, protein T cell media (pg/ml) vs. IL-8 (A) and LIF (B). Ruxolitinib co-cultured with the CD3/CD28-activated human CD8+ T cells reduced several additional mediators that are not obligated to use JAK1 signaling.

Figure 10:
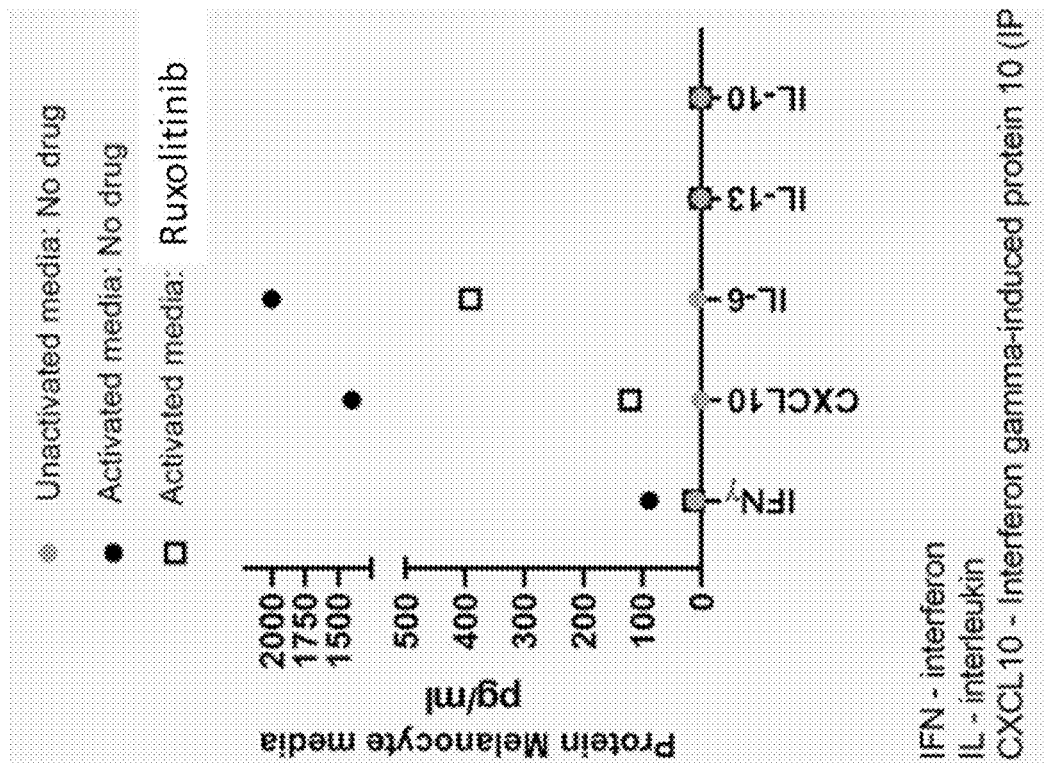
FIG. 10 is a graph depicting the effect of ruxolitinib on JAK1-dependent cytokines using melanocytes, protein melanocyte media (pg/ml) vs. specific JAK1-dependent cytokines.

FIG. 10 is a graph depicting the effect of ruxolitinib on JAK1-dependent cytokines using melanocytes, protein melanocyte media (pg/ml) vs. specific JAK1-dependent cytokines. Ruxolitinib reduces inflammatory cytokines that are JAK-STAT dependent (there appears to be no effect for inflammatory cytokines IL-13 and IL-10). Several of these cytokines are upregulated by melanocytes under stress conditions (IFNγ, CXCL10, IL-6).

Figure 11B:
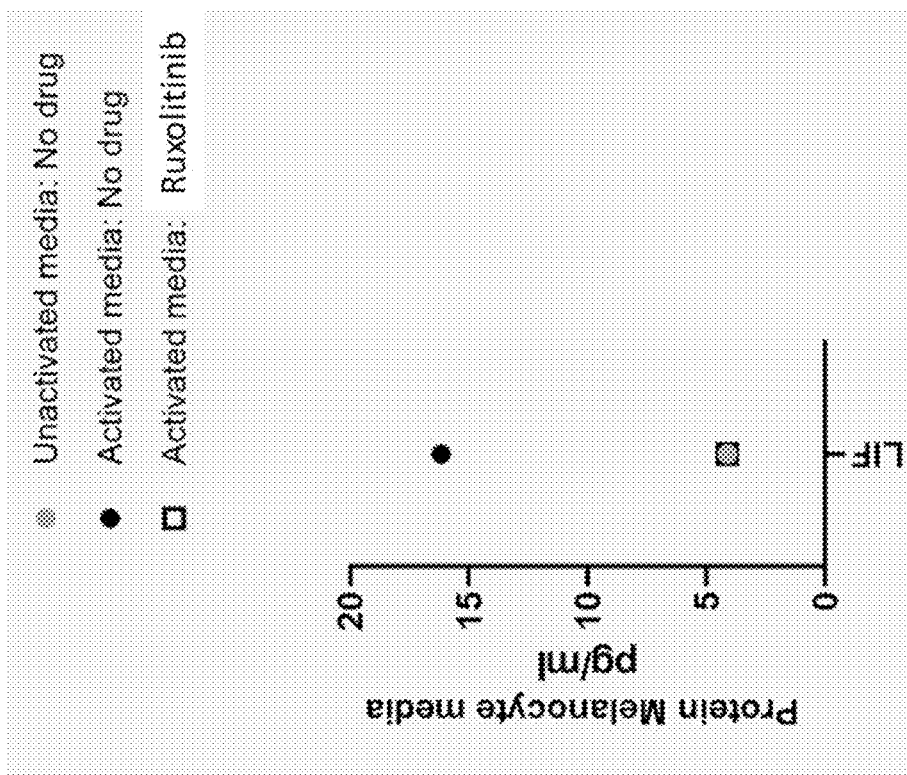
FIGS. 11A-B are graphs depicting the effect of ruxolitinib on growth factors and chemokine using melanocytes, protein melanocyte media (pg/ml) vs. IL-8 (A) and LIF (B).
Figure 11A:
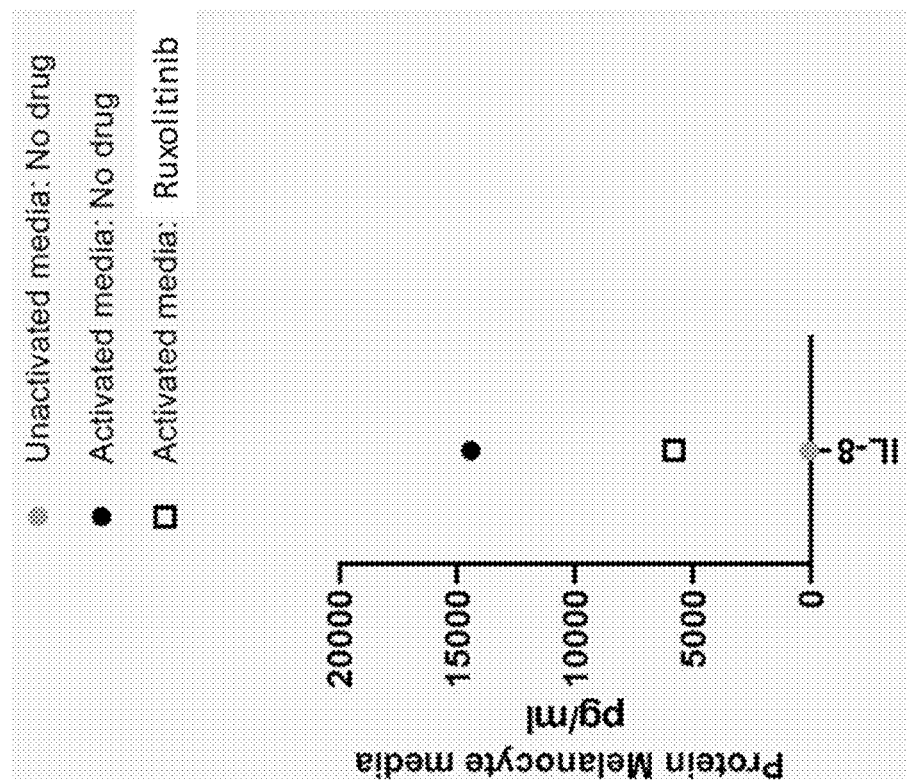

FIGS. 11A-B are graphs depicting the effect of ruxolitinib on growth factors and chemokine using melanocytes, protein melanocyte media (pg/ml) vs. IL-8 (A) and LIF (B). IL-8 is upregulated by melanocytes under stress conditions and this is reduced in ruxolitinib conditions.

Discussion: Interleukin-8 (IL-8/CXCL8) is reported to potentiate the proliferative response of melanocytes to multiple growth factors via binding to its cognate receptors (CXCR1 & CXCR2). IL-8 production and CXCR1/2 signaling are both JAK1 independent. Ruxolitinib treatment of CD8+ T cells slightly reduced IL-8 concentration.

Leukemia inhibitory factor (LIF) increases primary melanocyte proliferation and differentiation. LIF receptor signaling is JAK1-dependent and therefore ruxolitinib would be expected to have a detrimental effect on melanocyte proliferation. Unexpectedly, melanocyte proliferation is increased. Based on the data (T cells), on-target inhibition of LIF is not matched by enhanced melanocyte proliferation response.

Ruxolitinib can downregulate inflammatory cytokines in a CD8+ activated T cell microenvironment. It allows melanocyte proliferation to normalize and also stops the generation of inflammatory mediators from the melanocyte.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method for treating non-segmental vitiligo in a subject, said method comprising administering to the subject a therapeutically effective amount of JAK1 pathway inhibitor 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof, wherein the JAK1 pathway inhibitor, or pharmaceutically acceptable salt thereof is administered in a daily dose of about 10 mg to about 80 mg on a free base basis.

2. The method of claim 1, wherein the JAK1 pathway inhibitor is a pharmaceutically acceptable salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide.

3. The method of claim 1, wherein the JAK1 pathway inhibitor is 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide phosphoric acid salt.

4. The method of claim 1, wherein the JAM pathway inhibitor, or pharmaceutically acceptable salt thereof, is administered in combination with a further therapeutic agent.

5. The method of claim 4, wherein the further therapeutic agent comprises a Janus kinase inhibitor.

6. The method of claim 5, wherein the Janus kinase inhibitor comprises ruxolitinib, or a pharmaceutically acceptable salt thereof.

7. The method of claim 1, wherein the administering comprises administering the JAK1 pathway inhibitor, or pharmaceutically acceptable salt thereof, together with at least one pharmaceutically acceptable carrier or excipient.

8. The method of claim 1, wherein the JAK1 pathway inhibitor is 4-[(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide free base.

9. The method of claim 1, wherein the JAK1 pathway inhibitor, or pharmaceutically acceptable salt thereof, is administered in a daily dose of about 15 mg on a free base basis.

10. The method of claim 1, wherein the JAK1 pathway inhibitor, or pharmaceutically acceptable salt thereof, is administered in a daily dose of about 45 mg on a free base basis.

11. The method of claim 1, wherein the JAK1 pathway inhibitor, or pharmaceutically acceptable salt thereof, is administered in a daily dose of about 75 mg on a free base basis.

12. The method of claim 1, wherein the JAK1 pathway inhibitor, or pharmaceutically acceptable salt thereof, is administered in a daily dose of about 30 mg on a free base basis.

13. The method of claim 1, wherein the JAK1 pathway inhibitor, or pharmaceutically acceptable salt thereof, is administered in a daily dose of about 60 mg on a free base basis.

* * * * *

UNITED STATES PATENT AND TRADEMARK OFFICE
CERTIFICATE OF CORRECTION

PATENT NO. : 11,957,661 B2
APPLICATION NO. : 17/545377
DATED : April 16, 2024
INVENTOR(S) : Paul Smith et al.

It is certified that error appears in the above-identified patent and that said Letters Patent is hereby corrected as shown below:

In the Claims

Column 48, Line 11, Claim 3, delete "1H, 1′H" and insert -- 1H,1′H --;

Column 48, Line 14, Claim 4, delete "JAM" and insert -- JAK1 --;

Column 48, Line 28, Claim 8, delete "4-[(cyanomethyl)" and insert -- 4-[3-(cyanomethyl) --.

Signed and Sealed this
Sixth Day of August, 2024

*Katherine Kelly Vidal*
Katherine Kelly Vidal
*Director of the United States Patent and Trademark Office*